United States Patent
Bodinge et al.

(10) Patent No.: US 9,492,394 B2
(45) Date of Patent: Nov. 15, 2016

(54) GASTRIC RESISTANT PHARMACEUTICAL OR NUTRACEUTICAL FORMULATION COMPRISING ONE OR MORE SALTS OF ALGINIC ACID

(75) Inventors: Shraddha Ashok Bodinge, Thane (IN); Priyanka Bansilal Haksar, Thane West (IN); Seema Yashwant Gawde, Mumbai (IN); Hemant Karbhari Pagar, Nasik (IN); Hans-Ulrich Petereit, Darmstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 53 days.

(21) Appl. No.: 13/086,079

(22) Filed: Apr. 13, 2011

(65) Prior Publication Data
US 2012/0093926 A1 Apr. 19, 2012

(30) Foreign Application Priority Data
Aug. 18, 2010 (IN) .............................. 2378/CHE/2010

(51) Int. Cl.
*A61K 9/28* (2006.01)

(52) U.S. Cl.
CPC .............. *A61K 9/286* (2013.01); *A61K 9/2846* (2013.01); *A61K 9/2866* (2013.01)

(58) Field of Classification Search
None
See application file for complete search history.

(56) References Cited

U.S. PATENT DOCUMENTS

| | | | |
|---|---|---|---|
| 5,811,126 A * | 9/1998 | Krishnamurthy | .... A61K 9/2013 424/459 |
| 5,882,715 A | 3/1999 | Nielsen et al. | |
| 8,123,849 B2 * | 2/2012 | Rajsharad et al. | ....... 106/205.01 |
| 2002/0192284 A1 | 12/2002 | Moroni et al. | |
| 2003/0129235 A1* | 7/2003 | Chen et al. | ................... 424/470 |
| 2004/0253309 A1* | 12/2004 | Tanijiri et al. | ................. 424/469 |
| 2005/0239845 A1* | 10/2005 | Proehl et al. | ................. 514/338 |
| 2007/0071821 A1* | 3/2007 | Young | ............................ 424/470 |
| 2007/0104789 A1 | 5/2007 | Spector | |
| 2008/0107732 A1 | 5/2008 | Dharmadhikari et al. | |
| 2008/0220080 A1* | 9/2008 | Petereit | .................. A61K 9/209 424/497 |
| 2008/0274181 A1* | 11/2008 | Maes | ..................... A61K 9/284 424/472 |
| 2009/0028941 A1* | 1/2009 | Cowles et al. | ................ 424/469 |

FOREIGN PATENT DOCUMENTS

| | | |
|---|---|---|
| CN | 1938006 A | 3/2007 |
| CN | 101801357 A | 8/2010 |
| CN | 101888828 A | 11/2010 |
| JP | 61-207328 | 9/1986 |
| JP | 2004-249231 | 9/2004 |
| JP | 2007-530683 | 11/2007 |
| JP | 2010-522742 | 7/2010 |
| WO | WO 97/00674 | 1/1997 |
| WO | WO 02/098393 A1 | 12/2002 |
| WO | WO 2005/097082 A1 | 10/2005 |
| WO | WO 2005/101983 A2 | 11/2005 |
| WO | WO 2005/101983 A3 | 11/2005 |
| WO | WO 2009036812 A1 * | 3/2009 |

OTHER PUBLICATIONS

International Search Report ssued on Jul. 8, 2011 in PCT/EP 2011/055809 filed Apr. 13, 2011.
H. R. Bhagat, et al., "Kinetics and Mechanism of Drug Release From Calcium Alginate Membrane Coated Tablets", Drug Development and Industrial Pharmacy, vol. 20, No. 3, XP 000605822, Jan. 1, 1994, pp. 387-394.
Combined Chinese Office Action and Search Report issued May 30, 2014 in Patent Application No. 201180040052.6 (with English language translation).
Japanese Office Action issued Sep. 8, 2014, in Japan Patent Application No. 2013-524383 (with English translation).
Office Action issued in corresponding Russian Patent Application No. 2013111605/15 (017173), dated Mar. 18, 2015, with English translation (10 pp.).

* cited by examiner

Primary Examiner — Robert T Crow
Assistant Examiner — John P Nguyen
(74) Attorney, Agent, or Firm — Oblon, McClelland, Maier & Neustadt, L.L.P.

(57) ABSTRACT

The invention relates to a gastric resistant pharmaceutical or nutraceutical composition, comprising a core, comprising a pharmaceutical or nutraceutical active ingredient and a gastric resistant coating layer onto the core, wherein the release of the pharmaceutical or nutraceutical active ingredient is not more than 15% under in-vitro conditions at pH 1.2 for 2 hours in medium according to USP with and without the addition of 40% (v/v) ethanol, wherein the gastric resistant coating layer comprises 10 to 100% by weight of one or more salts of alginic acid with a viscosity of 30 to 720 cP of a 1% aqueous solution.

21 Claims, No Drawings

GASTRIC RESISTANT PHARMACEUTICAL OR NUTRACEUTICAL FORMULATION COMPRISING ONE OR MORE SALTS OF ALGINIC ACID

CROSS REFERENCE TO RELATED APPLICATIONS

This application claims priority to Indian Application No. 2378/CHE/2010, filed Aug. 18, 2010, the disclosure of which in incorporated herein by reference in its entirety.

BACKGROUND OF THE INVENTION

Technical Background

The study of Gürsoy A. and Cevik S., *J. Microencapsulation*, 2000, vol. 17, no. 5, 565-575 is focussed on the properties of diclofenac sodium (DNa) alginate microspheres and tabletted DNa alginate microspheres using different polymers as additives. DNa alginate microspheres were prepared by the emulsification method and different polymers such as EUDRAGIT® NE 30 D, EUDRAGIT® RS 30 D or different kinds of celluloses, which were incorporated into the alginate gel to control the release rate of the drug.

US 2007/053698 discloses methods of sustained release administration of opioids, including but not limited to hydromorphone and oxycodone, that exhibit improved properties with respect to co-ingestion with aqueous alcohol. Ethanol resistant matrix tablet compositions may comprise hydromorphone or oxycodone as active ingredients and mixtures of substances like EUDRAGIT® RS, Lactose, Mg-stearate, stearyl alcohol, carnauba wax and the like.

US 2007/0104789 A1 describes gastro-resistant and ethanol-resistant controlled-release formulations comprising hydromorphone. The gastro-resistant and ethanol-resistant can be used in a matrix as well as the coating of the formulations. Alginic acid is mentioned among the examples for suitable gastro-resistant and -ethanol resistant substances. Pellet cores or granules may be prepared by anhydrous granulation, may be coated with the gastro-resistant and ethanol-resistant substances and then may be filled in capsules or bags or compressed into tablets under addition of dried pharmaceutical or nutraceutically acceptable auxiliary substances.

Problem and Solution

Pharmaceutical or nutraceutical compositions are designed to release the active ingredient in a manner of reproducible release curves. This shall result in desirable and reliable blood level profiles which shall provide an optimal therapeutic effect. If the blood level concentrations are too low, the active ingredient will not cause a sufficient therapeutic effect. If the blood level concentrations are too high, this may cause toxic effects. In both cases non optimal blood level concentrations of an active ingredient can be dangerous for the patient and shall therefore be avoided. A problem exists in that the ideal ratios assumed for the release of active ingredient during the design of a pharmaceutical or nutraceutical composition can be altered by the general living habits, thoughtlessness or by addictive behaviour of the patients with respect to the use of ethanol or ethanol-containing drinks. In these cases, the pharmaceutical or nutraceutical form which is actually designed for an exclusively aqueous medium is additionally exposed to an ethanol containing medium of greater or lesser strength. Since health authorities like for instance the US Food and Drug Administration (FDA) focus more and more on the ethanol problem, ethanol resistance may be an important registration requirement in the near future.

Since not all patients are aware of the risk of simultaneous taking of a controlled release pharmaceutical or nutraceutical form and ethanol-containing drinks or do not follow or are not able to follow appropriate warnings, advice or recommendations, there is a demand for controlled release pharmaceutical or nutraceutical compositions, especially for gastric resistant pharmaceutical or nutraceutical compositions, such that their mode of action is affected as little as possible by the presence of ethanol.

Conventional gastric resistant pharmaceutical or nutraceutical compositions if coated or uncoated are usually not resistant to alcohol at all. Therefore one problem of the present invention was to provide gastric resistant pharmaceutical or nutraceutical compositions which are resistant against the influence of ethanol.

Especially there is a problem for gastric resistant or enteric formulated compositions. These kinds of formulations are usually coated with a gastric resistant coating layer (enteric coating layer) onto the core which has the function that the release of the pharmaceutical or nutraceutical active ingredient in the stomach, respectively at pH 1.2 for 2 hours according to USP, shall not exceed 10%, preferably less than 5%. This function ensures that acid-sensitive pharmaceutical or nutraceutical active ingredients are protected against inactivation and that pharmaceutical or nutraceutical active ingredients which may be irritate the stomach mucosa are not set free in too high amounts. On the other hand in many cases the release of the pharmaceutical or nutraceutical active ingredient in the intestine, respectively at pH 6.8 for one hour or less according to the USP method, is designed to exceed at least 70, 75% or more. The presence of ethanol in concentrations of 5, 10, 20 or 40% (volume/volume) in the gastric fluid usually leads to an increase to the release rates in the stomach. Due to distribution effect the effect of ingested ethanol is in the intestine not of that importance as in the stomach. Thus an effective protection against the influence of ethanol should prevent such an undesired increase of pharmaceutical or nutraceutical active ingredient in the stomach in the first place. Furthermore it may be desired that protection against the influence of ethanol shall at least not influence the comparably fast release rates at pH 6.8 in media without ethanol.

The Problem is Solved by a gastric resistant pharmaceutical or nutraceutical composition, comprising a core, comprising a pharmaceutical or nutraceutical active ingredient and a gastric resistant coating layer onto the core, wherein the release of the pharmaceutical or nutraceutical active ingredient is not more than 15, preferably not more than 10% under in-vitro conditions at pH 1.2 for 2 hours in medium according to USP with and without the addition of 40% (v/v) ethanol, wherein the gastric resistant coating layer comprises 10 to 100% by weight of one or more salts of alginic acid with a viscosity of 30 to 720 cP, preferably 40 to 450 cp, of a 1% aqueous solution.

DETAILED DESCRIPTION OF THE INVENTION

The invention relates to a gastric resistant pharmaceutical or nutraceutical composition, comprising a core, comprising a pharmaceutical or nutraceutical active ingredient and a gastric resistant coating layer onto the core.

Core

The core may comprise or may contain a neutral carrier pellet, for instance a sugar sphere or non-pareilles, on top of which the active ingredient is bound in a binder, such as lactose or polyvinylpyrrolidon. The core may alternatively comprise a pellet in the form of a polymeric matrix in which the active ingredient is bound. The core may comprise an uncoated pellet consisting of a crystallized active ingredient. The core may be as well a tablet, a mini tablet or a capsule.

The gastric resistant coating layer (enteric coating layer) onto the core has the function that the release of the pharmaceutical or nutraceutical active ingredient is not more than 15%, not more than 10%, not more than 8%, not more than 5% under in-vitro conditions at pH 1.2 for 2 hours in medium according to USP with and without the addition of 40% (v/v) ethanol. The USP (USP=United States Pharmacopoeia) which may be preferably used is USP32/NF27 (NF=National Formulary), apparatus II, paddle method, 50 rpm for tablets or paddle or basket method 50 to 100 rpm, depending on the monographie, for pellets.

Gastric Resistant Coating Layer

The gastric resistant coating layer comprises at least one or more salts of alginic acid and may further comprise water-insoluble polymers and/or pharmaceutical or nutraceutically acceptable excipients as described herein.

The gastric resistant coating layer onto the core may preferably further have the function that the release of the pharmaceutical or nutraceutical active ingredient is not more than 15%, not more than 10%, not more than 8%, not more than 5% under in-vitro conditions at pH 1.2 for 2 hours in medium according to USP with and without the addition of 5, 10, 20 or 40% (v/v) ethanol.

Release Rates at pH 6.8

The release of the pharmaceutical or nutraceutical active ingredient may be at least 50, at least 70, preferably at least 75%, most preferably at least 80% under in-vitro conditions at pH 6.8 for one hour, preferably for 45 minutes, in a buffered medium according to USP without the addition of 40% (v/v) ethanol.

Amounts of Coating Layer

The polymer dry weight gain of the coating layer may be at least 2.5, at least 3.5, at least 4, preferably 4 to 30, preferably 4 to 20, more preferably 5 to 18, or most preferably 10 to 18 mg/cm$^2$ surface area. This may correlate to 2-60% polymer dry weight gain related to the weight of the core. In the case of coated tablets the polymer dry weight gain related to the weight of the core (tablet core: around 1-25 or 1-10 mm in diameter or length) may be 2-30%. In the case of coated pellets the polymer dry weight gain related to the weight of the core (pellet core: 0.1 to 1.5 mm in diameter) may be 10-60%.

Very thin coatings with polymer weight gains of less than 4 mg/cm$^2$ are possible but may be sometimes difficult to realize and to reproduce. Promising results in this case may especially be achieved when potassium alginate is employed as the salt of alginic acid. However in general coatings of at least 4 mg/cm$^2$ polymer weight gain are recommended by the inventors and can be easily achieved with all kinds of salts of alginic acid.

Salts of Alginic Acid

The gastric resistant coating layer may comprise, may comprise essentially or may contain 10 to 100, 20 to 100, 30 to 100, 40 to 100, 50 to 100, preferably 60 to 95, more preferred 70 to 90% by weight of one or more salts of alginic acid.

The salts of alginic acid may be selected from sodium alginate, potassium alginate, magnesium alginate, lithium alginate or ammonium alginate or mixtures thereof.

Viscosity

The salts of alginic acid may have a viscosity of 30 to 720, preferably 40 to 450, preferably 40 to 400 or preferably 50 to 300 centipoise (cp) of a 1% aqueous solution (weight/weight).

The methodology of determination of the viscosity of a polymer solution, for instance a solution of a salt of alginic acid, is well known to the skilled person. The viscosity is preferably determined according to European Pharmacopeia 7$^{th}$ edition, general chapter 2, methods of analysis, 2.2.8 and 2.2.10, page 27ff. The test is performed using a spindle viscometer.

The viscosity of a 1% alginate solution may be determined by adding 3 g product to 250 ml of distilled water in a beaker while stirring at 800 rpm using overhead stirrer. Then additional 47 ml water was added with rinsing the walls of the beaker. After stirring for 2 hours and getting a complete solution, the viscosity is measured using a LV model of the Brookfield viscometer at 25° C. (77° F.) at 60 rpm with no. 2 spindle for samples with a viscosity of more than 100 cP and at 60 rpm with no. 1 spindle for samples with viscosity less than 100 cP. Since the weight of water is almost exactly 1 g/ml even at 25° C. "weight/weight" is regarded as equal or identical to "weight/volume" in the sense of the invention. Theoretically possible marginal differences are regarded as insignificant.

Addition of Further Polymers to the Gastric Resistant Coating Layer

The gastric resistant coating layer may comprise, essentially comprise or contain optionally 0 to 400, 0 to 300, 0 to 200, 0 to 100, 0 to 70, 0 to 50, preferably 5 to 80, 5 to 40 or most preferably 15 to 60 or 15 to 30% by weight of one or more water-insoluble polymers or one or more cellulosic polymers or mixtures thereof based on the weight of the one or more salts of alginic acid contained.

The one or more water-insoluble polymers or one or more cellulosic polymers may preferably contain not more than 12% by weight of monomer residues with ionic side groups, preferably not more than 12% by weight of monomer residues with cationic side groups.

The one or more water-insoluble polymers or one or more cellulosic polymers may preferably contain less than 5% by weight, preferably not more than 2% by weight, more preferably not more than 1 or 0.05 to 1% by weight, of monomer residues with anionic side groups.

Water-Insoluble Polymers

Water-insoluble polymers in the sense of the invention are polymers which do not dissolve in water or are only swellable in water over of the whole range of pH 1-14. Water-insoluble polymers may be at the same time polymers containing not more than 12% of monomer residues with ionic side groups, like for instance EUDRAGIT® NE/NM or EUDRAGIT® RL/RS polymers.

Other kinds of water-insoluble polymers in the sense of the invention may be vinyl copolymers like polyvinylacetate, including derivates of polyvinylacetate. The polyvinylacetate may be present in the form of a dispersion. One example is the type Kollicoat® SR 30 D (BASF), polyvinylacetate dispersion, stabilized with povidone and Na-laurylsulfate.

The water-insoluble polymers may preferably belong to the group of (meth)acrylate copolymers.

EUDRAGIT® NE 30D/EUDRAGIT® NM 30D-Type Polymers

The gastric resistant coating layer may comprise a water-insoluble copolymer which is a copolymer composed of free-radical polymerized units of more than 95% by weight, in particular to an extent of at least 98% by weight, preferably to an extent of at least 99% by weight, in particular to an extent of at least 99% by weight, more preferably to an extent of 100% by weight, of (meth)acrylate monomers with neutral radicals, especially $C_1$- to $C_4$-alkyl radicals. These kinds of polymers do not dissolve in water or are only swellable in water over of the whole range of pH 1-14.

Suitable (meth)acrylate monomers with neutral radicals are, for example, methyl methacrylate, ethyl methacrylate, butyl methacrylate, methyl acrylate, ethyl acrylate, butyl acrylate. Preference is given to methyl methacrylate, ethyl acrylate and methyl acrylate.

Methacrylate monomers with anionic radicals, for example acrylic acid and/or methacrylic acid, may be present in small amounts of less than 5% by weight, preferably not more than 2% by weight, more preferably not more than 1 or 0.05 to 1% by weight.

Suitable examples are neutral or virtually neutral (meth) acrylate copolymers composed of 20 to 40% by weight of ethyl acrylate, 60 to 80% by weight of methyl methacrylate and 0 to less than 5% by weight, preferably 0 to 2 or 0.05 to 1% by weight of methacrylic acid or any methacrylic acid (EUDRAGIT® NE 30D or EUDRAGIT® NM 30D type).

EUDRAGIT® NE 30D and Eudragit® NM 30D are dispersions containing 30% by weight of copolymers composed of free-radically polymerized units of 30% by weight of ethyl acrylate and 70% by weight of methyl methacrylate.

Preference is given to neutral or essentially neutral methyl acrylate copolymers which, according to WO 01/68767, have been prepared as dispersions using 1-10% by weight of a nonionic emulsifier having an HLB value of 15.2 to 17.3. The latter offer the advantage that there is no phase separation with formation of crystal structures by the emulsifier (Eudragit® NM 30D type).

According to EP 1 571 164 A2, corresponding, virtually neutral (meth)acrylate copolymers with small proportions of 0.05 to 1% by weight of monoolefinically unsaturated C3-C8-carboxylic acids can, however, also be prepared by emulsion polymerization in the presence of comparatively small amounts of anionic emulsifiers, for example 0.001 to 1% by weight.

EUDRAGIT® RL/RS-Type Polymers

The gastric resistant coating layer may comprise a water-insoluble copolymer which is a copolymer composed of free-radical polymerized units of 85 to 98% by weight of free-radical polymerized $C_1$ to $C_4$ alkyl esters of acrylic or methacrylic acid and 15 to 2% by weight of (meth)acrylate monomers with a quaternary amino group in the alkyl radical. These kinds of polymers do not dissolve in water or are only swellable in water over of the whole range of pH 1-14.

Cellulosic Polymers

Suitable polymers may also belong to the group of cellulosic polymers, preferably to the group of water soluble celluloses. The cellulosic polymer is preferably a water-soluble cellulose. A suitable cellulosic polymer is hydroxypropylmethyl cellulose (HPMC).

Pharmaceutical or Nutraceutical Active Ingredient
Nutraceuticals

The invention is preferably useful for nutraceutical dosage forms.

Nutraceuticals can be defined as extracts of foods claimed to have medical effects on human health. The nutraceutical is usual contained in a medical format such as capsule, tablet or powder in a prescribed dose. Examples for nutraceuticals are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flavonoids, antioxidants, alpha-linoleic acid from flax seed, beta-carotene from marigold petals or antocyanins from berries. Sometimes the expression neutraceuticals is used as synonym for nutraceuticals. The gastric resistant pharmaceutical or nutraceutical composition is comprising a core, comprising a pharmaceutical or nutraceutical active ingredient. The pharmaceutical or nutraceutical active ingredient may be a pharmaceutical or nutraceutical active ingredient which may be inactivated under the influence of gastric fluids at pH 1.2 or a pharmaceutical or nutraceutical active ingredient which may irritate the stomach mucosa when set free in the stomach.

Pharmaceutical Active Ingredients

The invention is also preferably useful for enteric coated pharmaceutical dosage forms.

Therapeutical and chemical classes of drugs used in enteric coated pharmaceutical dosage forms are for instance analgetics, antibiotics or anti-infectives, antibodies, antiepileptics, antigens from plants, antirheumatics, betablocker, benzimidazole derivatives, beta-blocker, cardiovascular drugs, chemotherapeuitcs, CNS drugs, digitalis glycosides, gastrointestinal drugs, e.g. proton pum inhibitors, enzymes, hormones, liquid or solid natural extracts, oligonucleotides, peptidhormon proteins, therapeutical bacteria, peptides, proteins, proton pump inhibitors, (metal) salt f.e. aspartates, chlorides, orthates, urology drugs, vaccines Examples of drugs, which are acid-lablile, irritating or need controlled release, may be: Acamprosat, aescin, amylase, acetylsalicylic acid, adrenalin, 5-amino salicylic acid, aureomycin, bacitracin, balsalazine, beta carotene, bicalutamid bisacodyl, bromelain, bromelain, budesonide, calcitonin, carbamacipine, carboplatin, cephalosporins, cetrorelix, clarithromycin, chloromycetin, cimetidine, cisapride, cladribine, clorazepate, cromalyn, 1-deaminocysteine-8-D-arginine-vasopressin, deramciclane, detirelix, dexlansoprazole, diclofenac, didanosine, digitoxin and other digitalis glycosides, dihydrostreptomycin, dimethicone, divalproex, drospirenone, duloxetine, enzymes, erythromycin, esomeprazole, estrogens, etoposide, famotidine, fluorides, garlic oil, glucagon, granulocyte colony stimulating factor (G-CSF), heparin, hydrocortisone, human growth hormon (hGH), ibuprofen, ilaprazole, insulin, Interferon, Interleukin, Intron A, ketoprofen, lansoprazole, leuprolidacetat lipase, lipoic acid, lithium, kinin, memantine, mesalazine, methenamine, milameline, minerals, minoprazole, naproxen, natamycin, nitrofurantion, novobiocin, olsalazine, omeprazole, orothates, pancreatin, pantoprazole, parathyroidhormone, paroxetine, penicillin, perprazol, pindolol, polymyxin, potassium, pravastatin, prednisone, preglumetacin progabide, pro-somatostatin, protease, quinapril, rabeprazole, ranitidine, ranolazine, reboxetine, rutosid, somatostatin streptomycin, subtilin, sulfasalazine, sulphanilamide, tamsulosin, tenatoprazole, thrypsine, valproic acid, vasopressin, vitamins, zinc, including their salts, derivatives, polymorphs, isomorphs, or any kinds of mixtures or combinations thereof.

Gastric Resistant Pharmaceutical or Nutraceutical Composition

The gastric resistant pharmaceutical or nutraceutical composition may be a coated tablet, a coated minitablet, a coated pellet, a coated granule, a sachet, a capsule, filled with coated pellets or with powder or with granules, or a coated capsule, filled with coated pellets or with powder or with granules.

The term coated tablet includes pellet-containing tablets or compressed tablets and is well known to a skilled person. Such a tablet may have a size of around 5 to 25 mm for instance. Usually, defined pluralities of small active ingredient containing pellets are compressed therein together with binding excipients to give the well known tablet form. After oral ingestion and contact with the body fluid the tablet form is disrupted and the pellets are set free. The compressed tablet combines the advantage of the single dose form for ingestion with the advantages of a multiple forms, for instance the dosage accuracy.

The term coated minitablet is well known to the skilled person. A minitablet is smaller than the traditional tablet and may have a size of around 1 to 4 mm. The minitablet is, like a pellet, a single dosage form to be used in multiple dosages. In comparison to pellets, which may be in the same size, minitablets usually have the advantage of having more regular surfaces which can be coated more accurately and more uniformly. Minitablets may be provided enclosed in capsules, such as gelatine capsules. Such capsules disrupt after oral ingestion and contact with the gastric or intestinal fluids and the minitablets are set free. Another application of minitablets is the individual fine adjustment of the active ingredient dosage. In this case the patient may ingest a defined number of minitablets directly which matches to the severe of the decease to cure but also to his individual body weight. A minitablet is different from pellet-containing compressed tablet as discussed above.

The term sachet is well known to the skilled person. It refers to small sealed package which contains the active ingredient often in pellet containing liquid form or also in dry pellet or powder form. The sachet itself is only the package form is not intended to be ingested. The content of the sachet may be dissolved in water or as an advantageous feature may be soaked or ingested directly without further liquid. The latter is advantageous feature for the patient when the dosage form shall be ingested in a situation where no water is available. The sachet is an alternative dosage form to tablets, minitablets or capsules.

Coated pellets may be filled in a capsule, for instance gelatine or HPMC capsule. A capsule containing pellets may also be coated with the enteric coating layer according to the invention.

The gastric resistant pharmaceutical or nutraceutical composition is preferably present in the form of an aqueous coating solution, suspension or dispersion. The dry weight content of the solution, suspension or dispersion may be in the range of 10 to 50, preferably 15 to 35%.

Pharmaceutical or Nutraceutically Acceptable Excipients

A gastric resistant pharmaceutical or nutraceutical composition may optionally comprise in the gastric resistant coating layer up to 90, up to 80, up to 70, up to 60, up to 50, up to 40, up to 30, up to 20, or up to 10% by weight of pharmaceutical or nutraceutically acceptable excipients. The pharmaceutical or nutraceutically acceptable excipients are different from salts of alginic acid and different from the water-insoluble polymers or the cellulosic polymers mentioned above and may be selected from the group of antioxidants, brighteners, binding agents, flavouring agents, flow aids, fragrances, glidants, penetration-promoting agents, polymers (different from salts of alginic acid and different from the water-insoluble polymers or the cellulosic polymers mentioned above; excipient polymers can be for instance disintegrants like crosslinked polyvinyl pyrrolidone), pigments, plasticizers, pore-forming agents or stabilizers or combinations thereof.

Process for Producing a Pharmaceutical or Nutraceutical Form

The invention further relates to a process for producing the pharmaceutical or nutraceutical form according of the invention by forming the core comprising the active ingredient by direct compression, compression of dry, wet or sintered granules, extrusion and subsequent rounding off, wet or dry granulation or direct pelleting or by binding powders (powder layering) onto active ingredient-free beads or neutral cores (nonpareilles) or active ingredient-containing particles and by applying the polymer coating in the form of an aqueous dispersion in a spray process or by fluidized bed spray granulation onto the core.

Top Coat and Sub Coats

The gastric resistant pharmaceutical or nutraceutical composition according to the invention may be further coated with a sub coat or a top coat or both.

A sub coat may be located between the core and the gastric resistant (enteric) coating layer. A sub coat may have the function to separate substances of the core from substances of the controlling layer which may be incompatible with each other. The sub coat has essentially no influence on the active ingredient release characteristics. A subcoat is preferably essentially water-soluble, for instance it may consist of substances like hydroxypropylmethyl-cellulose (HPMC) as a film former. The average thickness of the subcoat layer is very thin, for example not more than 15 μm, preferably not more than 10 μm.

A top coat is also preferably essentially water soluble. A top coat may have the function of colouring the pharmaceutical or nutraceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical or nutraceutical excipients like pigments or glidants in high amounts. The topcoat has essentially no influence on the release characteristics.

The expressions sub coat and top coat are well known to the person skilled in the art.

Pellets/Tablets

As a rough estimation coated pellets may have a size in the range of 50 to 1000 μm (average diameter), while coated tablets may have a size in the range of above 1000 μm up to 25 mm (diameter or length). As a rule one can say the smaller the size of the pellet cores are, the higher the pellet coating weight gain needed. This is due to the comparably higher surface area of pellets compared to tablets.

In coatings for pellets also comparably high amounts of excipients, preferably talcum, may be used in contrast to coating for tablet. Amounts of more than 50 and up to 250% by weight in relation to the amount of the salt of alginic acid may be used which may correspond to more than 50 and up to 90% by weight of the coating layer.

In tablets coatings comparably low amounts of excipients, preferably talcum but also other excipients, may be used in contrast to pellets. Amounts of more 50 to 100% by weight in relation to the amount of the salt of alginic acid may be used which may correspond up to 50% by weight of the coating layer.

Ammonium Alginate (NH₄-Alginate)

One further embodiment of the present invention is the use of ammonium alginate as a substitute for or incombination with sodium alginate in situations were considerable amounts calcium ions are present in the food ingested together with the inventive gastric resistant pharmaceutical or nutraceutical composition. This can happen when diary products such like milk or yoghurt are consumed. Surprisingly it has been found that the presence of calcium ion in USP buffer pH 6.8 has almost no influence on the release rate of coatings in which ammonium alginate is used as the alginate salt. However the release rate at pH 6.8 of coatings in which sodium alginate is used as the alginate salt drops down almost totally (s. examples 32-37).

Coating

Coating suspensions are applied by spray coating processes following known processes. As a rule the coated compositions are cured at elevated temperatures for example 24 hours at 40° C. or 60° C. after the spray coating in order to provide reproducible and stable functionality. Surprisingly it was found that pure aliginate coatings do not need any curing to reach reproducible and stable functionality. Therefore pure alginate coatings in the examples were not cured. However when aliginate is mixed with one or more water-insoluble polymers or one or more cellulosic polymers the coated formulations had to be cured after the spraying process.

More than One Gastric Resistant Coating Layer (Double or Multilayer Coatings)

In certain embodiments it may be useful to have two or more different gastric resistant coatings layers. In example 40 a pellet coating shows an inner coating layer with a high content of talc and a disintegrant. The outer coating has a high content of talc but no disintegrant. In this case the inner coating accelerates the drug release in pH 6.8 buffer without affecting the enteric properties at pH 1.2. The outer coating alone would not show these combination of properties.

Examples 1C to 29C Overview

| No. | Alginate Quantity [mg/cm²] | Second Polymer [mg/cm²] EUDRAGIT® NM 30 D | NE 30 D | RS 30 D | Others | % Alg. | Result | Remark |
|---|---|---|---|---|---|---|---|---|
| | | Sodium Alginate <10 cP, PROTONAL® LFR 5/60 | | | | | | |
| 1. C | 8 | — | — | — | — | 100 | Not enteric | Low viscosity |
| 2. C | 12 | 4 | — | — | — | 75 | Not enteric | Low viscosity |
| | | Sodium Alginate 40-90 cP, Manucol® DH | | | | | | |
| 3. | 6 | — | — | — | — | 100 | + | +alco buffer |
| 4. | 12 | — | — | — | HPMC 6 cP 4 | 75 | ++ | |
| 5. | 13.3 | 2.7 | — | — | — | 83 | ++ | |
| 6. | 12.8 | 3.2 | — | — | — | 80 | ++ | |
| 7. | 12 | 4 | — | — | — | 75 | ++ | +alco buffer |
| 8. | 12 | — | 4 | — | — | 75 | ++ | |
| 9. | 12 | — | — | — | Kollicoat® SR 30 D 4 | 75 | ++ | |
| 10. | 12 | — | — | 4 | — | 75 | ++ | |
| 11 | 37.5% | 12.5% | — | — | — | 75 | ++ | Pellets |
| | | Sodium Alginate not less than 45 cP, Loba Chemie, Food Grade | | | | | | |
| 12. | 4 | — | — | — | — | 100 | + | |
| 13 | 2 | 4 | — | — | — | 33 | + | Slow rel..in buffer pH 6.8 |
| | | Potassium Alginate 200-400 cP PROTANAL® KF200 FTS | | | | | | |
| 14. C | 2 | — | — | — | — | 100 | Not enteric | Coating only 2 mg/cm2 |
| | | Sodium Alginate 50-150 cP, Keltone® LVCR | | | | | | |
| 15. | 4 | — | — | — | — | 100 | (+) | resistant > 20% alc. |
| 16. | 12 | 4 | — | — | — | 75 | ++ | |
| | | Sodium Alginate 70-200 cP, PROTANAL® LF 240 D | | | | | | |
| 17. | 4 | — | — | — | — | 100 | + | |
| 18 C | 3 | — | — | — | — | 100 | Not enteric | |
| 19. | 12 | 4 | — | — | — | 75 | ++ | |
| | | Potassium Alginate 200-400 cP PROTANAL® KF200 FTS | | | | | | |
| 20 | 3 or 4 | — | — | — | — | 100 | + | |
| 21 | 5.25 | 1.75 | — | — | — | 75 | ++ | |

| No. | Alginate Quantity [mg/cm²] | NM 30 D | NE 30 D | RS 30 D | Others | % Alg. | Result | Remark |
|---|---|---|---|---|---|---|---|---|
| Sodium Alginate 300-450 cP, KELTONE® HVCR | | | | | | | | |
| 22. | 6 | — | — | — | — | 100 | + | |
| 23. | 8 | — | — | — | — | 100 | ++ | |
| 24. | 9 | 3 | — | — | — | 75 | ++ | |
| Others | | | | | | | | |
| 25. C | — | — | — | — | Carageenan 10 | — | Not enteric | |
| 26. C | — | — | — | — | Alginic Acid 4 | — | Not enteric | |
| 27. C | — | 4 | — | — | Alginic Acid 12 | — | Not enteric | |
| 28. C | — | — | — | — | EUDRAGIT® L 30 D-555 | — | Not resistant | |
| 29 C | — | 4 | — | — | — | — | Not resistant | |

Legend for the table "Examples Overview"
+ = release in HCl pH 1.2 is 15% or less after 2 h with and without 5, 10, 20 and 40% EtOH
++ = release in HCl pH 1.2 is 5% or less after 2 h with and without 5, 10, 20 and 40% EtOH
Not enteric: release in HCl pH 1.2, 2 h, is more than 15% without EtOH
Not resistant: release in HCl pH 1.2, 2 h, is more than 15% with EtOH
+alco buffer = release data after 2 h test in HCl pH 1.2 is in buffer pH 6.8 after 1 h 70% or more with 5, 10, 20 and 40% EtOH
Example numbers with C = Comparative examples

EXAMPLES

All excipients meet pharmacopoeial or equivalent specifications.

Preparation of Tablet Cores

Formula for Tablet Preparation:

1) All ingredients were sifted through 40 mesh sieve (425 microns) and weighed accurately.
2) Microcrystalline cellulose (Avicel®101 and Avicel®200) and Povidone K-30 were mixed together in a polybag.
3) The sifted drug was gradually mixed with the above blend.
4) Talc was added to the above blend and mixed for 5 minutes in a cone blender.
5) The loss on drying for the blend was checked on a moisture balance. (If LOD was more than 2% w/w then blend should be dried in a tray dryer at 40° C. till the LOD is below 2% w/w.)
6) The blend from step 4 was lubricated with Magnesium stearate in a cone blender for 2 minutes.
7) The blend was compressed on a 16 station rotary compression machine using 11 mm circular standard concave punches Tablet parameters:

| Sr. No. | Tests | Values |
|---|---|---|
| 1. | Weight of tablet (in mg) | 400 ± 3% |
| 2. | Hardness | 8-9 Kg/cm² |
| 3. | Friability(at 500 rpm) | <1% |
| 4. | Thickness of tablets | 4.75 ± 0.1 mm |
| 5. | Disintegration time | <1 minute |

Coating Process

Equipment and Coating Parameters for Tablets:
Coating pan 12" with 3 baffles: Rotation 16-23 rpm
Silicone tube: 3.0 mm inner diameter
Spray rate: 1.5 gm/min–3 gm/min
Spray air pressure: 1 bar
Inlet air temperature: 50° C.
Product temperature: 30° C.-35° C.

Equipment and Coating Parameters for Pellets:
Instrument used: GPCG 3.1
Silicone tube: 3.0 mm inner diameter
Column height: 10-15 mm
Nozzle bore: 0.8 bar
Filter shaking: 10 sec
Filter shaking pause: 120 sec
Air flow mode: Auto
Air flow: 150 m³/h
Atomisation pressure: 1.2-1.5 bar
Inlet temperature: 60-65° C.
Product temperature: 50° C.-55° C.
Spray rate: 3-5 g/min Alginic Acid and Salts Used in Examples

| Commercial Name | Supplier | Viscosity Specification | Viscosity certified [cP] | Calculated Viscosity for 1% solution comparative |
|---|---|---|---|---|
| Sodium Alginates | | | | |
| PROTANAL® LFR 5/60 | FMC Biopolymers | 300-700 cP for 10% w/w solution | 490 | Less than 10 cP for 1% w/w solution |

-continued

| Commercial Name | Supplier | Viscosity Specification | Viscosity certified [cP] | Calculated Viscosity for 1% solution comparative |
|---|---|---|---|---|
| MANUCOL ® DH | FMC Biopolymers | 40-90 cP for 1% w/w solution | 68.5 | 40-90 cP for 1% w/w solution |
| Sodium alginate (Food grade) | Loba chemie | Not less than 45 cP | Not less than 45 | Not less than 45 cP |
| KELTONE ® LVCR | FMC Biopolymers | 100-300 cP for 2% w/w solution | 246 | 50-150 cP for 1% w/w solution |
| PROTANAL ® LF 240 D | FMC Biopolymers | 70-150 cP for 1% w/w solution | 86 | 70-150 cP for 1% w/w solution |
| KELTONE ® HVCR | FMC Biopolymers | 600-900 cP for 1.25% w/w solution Potassium alginate | 688 | 480-720 cP for 1% w/w solution |
| PROTANAL ® KF 200 FTS | FMC Biopolymers | 200-400 cP for 1% w/w solution Ammonium Alginate | 280 | 200-400 cP for 1% w/w solution |
| ALGIN ® NH-LV | KIMICA | 250-550 cP at 1% w/w solution | | 250-550 cP at 1% |

Analytical Methodology for Tablets
1. Dissolution Testing:
a) Acid Stage
Apparatus: USP Type II
Dissolution Medium: 0.1N HCl
Volume of Medium: 750 ml
Speed: 50 rpm
Temperature: 37° C.±0.5° C.
Withdrawal Volume: 10 ml
Time: 120 minutes
b) Buffer Stage
Apparatus: USP Type II
Dissolution Medium: Buffer stage medium pH 6.8
Volume of Medium: 1000 ml
Speed: 50 rpm
Temperature: 37° C.±0.5° C.
Withdrawal Volume: 10 ml
Time Points: 60 minutes (30, 45, 60 minutes)
Buffer Stage Medium:
Accurately weigh and transfer 19.01 g of Trisodium Phosphate and 6.37 mL of conc. hydrochloric acid to 1000 mL water. Dissolve and make up the volume to one liter and mix well. Adjust pH to 6.8±0.05 using 2N NaOH or 2N HCl.
2. Method of Detection-HPLC
Chromatographic Conditions
Column: Agilent Zorbax Eclipse XDB C8 column, 150×4.6 mm, 5 μm or equivalent
Mobile Phase: Water: Acetonitrile: (80:20)
Wavelength: 273 nm
Column Temp: 30° C.
Injection Volume: 10 μL
Flow rate: 1 mL/minute
Run time: 5 minutes
Standard Preparation:
Standard stock preparation—Weigh accurately and transfer about 50 mg of Caffeine standard into a 100 mL volumetric flask. Dissolve and make up the volume with water.
Acid Stage standard: Dilute 5 mL of stock solution to 50 mL with 0.1N HCl. Buffer Stage standard: Dilute 5 mL of stock solution to 50 mL with buffer stage medium.
Procedure:
Acid Stage: Weigh and transfer tablet of caffeine in six different dissolution jars and then perform the dissolution test as per parameters given in the method above (Acid Stage). After 2 hr remove 10 mL of aliquot and analyse as acid stage sample solution.
Buffer Stage: Transfer tablet to buffer stage medium pH 6.8. Continue the dissolution test as per parameters given in the method above (Buffer Stage). Filter the aliquots of each interval through 0.45 μm nylon membrane syringe filter discarding first few mL of the filtrate. Analyse buffer stage sample solution.
3. Disintegration Method:
1) Acid Stage
Apparatus: Disintegration tester
Dissolution Medium: SGF with pepsin, USP/NF
Volume of Medium: 900 ml
Temperature: 37° C.±0.5° C.
Time: 60 minutes
2) Buffer Stage
Apparatus: Disintegration tester
Dissolution Medium: SIF with pancreatin, USP/NF
  Volume of Medium: 900 ml
  Temperature: 37° C.±0.5° C.
Time: 60 minutes
Preparation of Simulated Gastric Fluid (SGF) with Pepsin, USP/NF
Accurately weigh and transfer 2.0 g of Sodium Chloride and 2.67 g of purified pepsin (that is derived from porcine stomach mucosa, with an activity of 3000 units per mg of protein) to 500 mL water. Dissolve the salts and to this add 7.0 mL of Hydrochloric acid and make up the volume to 1000 mL with water. This test solution has a pH of about 1.2.
Preparation of Simulated Intestinal Fluid (SIF) with Pancreatin, USP/NF:
Accurately weigh and transfer 6.8 g of monobasic potassium phosphate and 0.61 g of Sodium hydroxide and dissolve in 500 mL of water. To this add 10 g pancreatin, mix and adjust the resulting solution with either 0.2N sodium hydroxide or 0.2N hydrochloric acid to a pH of 6.8±0.1. Dilute with water to 1000 mL.
Alcohol (Ethanol) Study:
1) Dissolution Parameters
Apparatus: USP Type II
Dissolution Medium: 5%, 10%, 20% and 40% alcohol (ethanol) in 0.1N HCl.
Volume of Medium: 750 ml Speed: 50 rpm
Temperature: 37° C.±0.5° C.
Withdrawal Volume: 10 ml
Time: 2 hours
Method of Detection-HPLC: same as given for dissolution.
Standard Preparation:
Standard stock preparation—Weigh accurately and transfer about 50 mg of Caffeine standard into a 100 mL volumetric flask. Dissolve and make up the volume with water.
Alcohol standard: Dilute 5 mL of stock solution to 50 mL with respective alcoholic medium.
Procedure:
Weigh and transfer tablet of caffeine in six different dissolution jars and then perform the dissolution test as per parameters given in the method above (Alcohol). After 2 hr remove 10 mL of aliquot and analyse as alcohol sample solution. Filter the aliquots with 0.45 µm nylon membrane syringe filter discarding first few mL of the filtrate. Analyse alcohol sample solution.
Analytical Methodology for Lansoprazole Pellets
1. Dissolution Testing:
a) Acid Stage
Apparatus: USP Type II
Dissolution Medium: 0.1N HCl
Volume of Medium: 500 ml
Speed: 75 rpm
Temperature: 37° C.±0.5° C.
Withdrawal Volume: 25 ml
Time: 60 minutes
Detection Wavelength: 306 nm
b) Buffer Stage
Apparatus: USP Type II
Dissolution Medium: Buffer stage medium pH 6.8 (Refer note below)
Volume of Medium: 900 ml
Speed: 75 rpm
Temperature: 37° C.±0.5° C.
Withdrawal Volume: 10 ml
Time Points: 75 minutes (30, 45, 60, 75 minutes)
Detection Wavelength: Difference between absorbance at 286 nm and 650 nm
Buffer Stage Medium:
Buffer stage medium is a mixture of acid stage medium (475 mL) and phosphate buffer concentrate (425 mL) with pH adjusted to 6.8.
Preparation of Phosphate buffer Concentrate—
Accurately weigh 16.3 g of monobasic sodium Phosphate, 7.05 g of sodium hydroxide, 3.0 g of Sodium dodecyl sulfate and dissolve it water and make up the volume till one liter and mix well.
Procedure:
Acid Stage: Weigh and transfer pellets of lansoprazole (equivalent to 30 mg) in six different dissolution jars and then perform the dissolution test as per parameters given in the method above (Acid Stage). After 1 hr remove 25 mL of aliquot and analyse as acid stage sample solution.
Buffer Stage: Add 425 mL of Phosphate buffer concentrate to the acid stage medium (Buffer Stage—This will provide total of 900 mL pH 6.8 medium). Continue the dissolution test as per parameters given in the method above. Filter the aliquots of each interval through 0.45 µm nylon membrane syringe filter discarding first few mL of the filtrate. Analyse buffer stage sample solution.

Analytical Methodology for Caffeine Pellets
Analytical method for tablets has been used for Caffeine pellets Example 1C (Comparative)

Sodium Alginate (Less than 10 cP in 1% Aqueous Solution)

Coating of 8 mg/cm² polymer plain sodium alginate
Formula for polymer coating suspension on 300 g tablets.

| Ingredient | Manufacturer | Quantity/Batch [g] | Solid content [g] |
|---|---|---|---|
| PROTANAL ® LFR 5/60 (7% solution in water) | FMC Biopolymers | 428.6 | 30.0 |
| Talc | Luznac | 15.0 | 15.0 |
| Yellow iron oxide | BASF | 0.2 | 0.2 |
| Purified Water | | 457.9 | |
| Total | | 901.7 | 45.2 |

Procedure for coating suspension preparation:
　Sodium Alginate was weighed and kept under stirring with water for 30 minutes on an overhead stirrer to prepare 7% solution.
　Talc and colour were homogenized with remaining amount of water for 30 minutes.
　Homogenized talc suspension was added to Alginate solution and stirring was continued for further 30 mins.
　The final prepared suspension was passed through a sieve of 300 microns (60#).
　This suspension was further sprayed onto tablets in a coating pan.
Coating:
Coating continued up to 8 mg/cm² polymer
Suspension applied: 639.8 g
Curing parameter: No curing
Results:
　Yellow coloured tablets with smooth surface
　Enteric protection was not achieved up to 8 mg/cm² coating level with 94% drug release in 0.1 N HCl.

Example 2C (Comparative)

Sodium Alginate (Less than 10 cP in 1% Aqueous Solution

Coating of 16 mg/cm² polymer (EUDRAGIT® NM 30D 4 mg/cm²+sodium alginate 12 g/cm²)
Formula for Polymer Coating Suspension on 300 g Tablets.

| Ingredient | Manufacturer | Quantity/Batch [g] | Solid content [g] |
|---|---|---|---|
| PROTANAL ® LFR 5/60 (10% solution in water) | FMC Biopolymers | 450.0 | 45.0 |
| EUDRAGIT ® NM 30D | Evonik industries | 50.0 | 15.0 |

-continued

| Ingredient | Manufacturer | Quantity/Batch [g] | Solid content [g] |
|---|---|---|---|
| Talc | Luznac | 7.5 | 7.5 |
| Yellow iron oxide | BASF | 0.1 | 0.1 |
| Purified Water | | 168.2 | |
| Total | | 675.8 | 67.6 |

Procedure for Coating Suspension Preparation:
Sodium Alginate was weighed and kept under stirring with water for 30 minutes on an overhead stirrer to prepare 10% solution.
pH of sodium alginate was raised to 10 by addition of 25 ml of 0.1 N NaOH.
Talc and colour were homogenized with remaining amount of water for 30 minutes.
Homogenized talc suspension and EUDRAGIT® NM 30D were added to Alginate solution of step 2 and stirring was continued for further 30 mins.
The final prepared suspension was passed through a sieve of 300 microns (60#).
This suspension was further sprayed onto tablets in a coating pan.

Coating:
Coating continued up to 32 mg/cm² polymer, Suspension applied: 956.76 g
Curing parameter: 24 hrs at 60° C. in a tray dryer.
Results:
Yellow coloured tablets with smooth surface
Enteric protection was not achieved up to 32 mg/cm² coating level with 96.1% drug release in 0.1 N HCl.

Example 3

Sodium Alginate (40-90 cP in 1% Aqueous Solution)

Coating of 6 mg/cm² polymer plain sodium alginate
Formula for Coating Suspension on 300 g Tablets

| Ingredient | Manufacturer | Quantity/Batch [g] | Solid content [g] |
|---|---|---|---|
| MANUCOL ® DH (5% solution in water) | FMC Biopolymers | 300.0 | 15.0 |
| Talc | Luznac | 7.5 | 7.5 |
| Yellow iron oxide | BASF | 0.1 | 0.1 |
| Purified Water | | 256.9 | |
| Total | | 564.5 | 22.6 |

Procedure for Coating Suspension Preparation:
Sodium Alginate was weighed and kept under stirring with water for 30 minutes on an overhead stirrer to prepare 5% solution.
Talc and colour were homogenized with remaining amount of water for 30 minutes.
Homogenized talc suspension was added to Alginate solution of step 2 and stirring was continued for further 30 mins.
The final prepared suspension was passed through a sieve of 300 microns (60#).
This suspension was further sprayed onto tablets in a coating pan.

Coating:
Coating done up to 6 mg/cm² coating level
Suspension applied: 564.5 g
Curing parameter: No curing
Results:
Appearance—Yellow coloured tablets with smooth surface
Enteric protection was achieved with 6.1% drug release in 0.1N HCl for 5 mg/cm² coating level
Enteric protection was achieved with 6.4% drug release in 0.1N HCl for 6 mg/cm² coating level
82%, 89% and 91% drug release was observed in 30, 45 and 60 minutes respectively in USP pH 6.8 buffer with 5 mg/cm² coating level.
82%, 90% and 92% drug release was observed in 30, 45 and 60 minutes respectively in USP pH 6.8 buffer with 6 mg/cm² coating level.
Resistance to alcohol dose dumping was also observed with 5 mg/cm² as well 6 mg/cm² coating level at 5%, 10%, 20% and 40% alcohol levels.

| | Release [%] after 2 hr. in alcoholic HCl-Plain Na-Alginate | |
|---|---|---|
| Coating | 5% Alco HCl | 10% Alco HCl |
| 5 mg/cm² | 6.5% | 7% |
| 6 mg/cm² | 5% | 5% |
| Coating | 20% Alco HCl | 40% Alco HCl |
| 5 mg/cm² | 8% | 6% |
| 6 mg/cm² | 5% | 4% |

| Coating 6 mg/cm² | Release [%] after 2 hr. in alcoholic HCl followed by buffer pH 6.8 | |
|---|---|---|
| Time | 5% Alcoholic HCl followed by buffer pH 6.8 | 10% Alcoholic HCl followed by buffer pH 6.8 |
| 30 min | 82.8 | 83.6 |
| 45 min | 88.3 | 86.2 |
| 60 min | 89.9 | 87.7 |
| Time | 20% Alcoholic HCl followed by buffer pH 6.8 | 40% Alcoholic HCl followed by buffer pH 6.8 |
| 30 min | 85.5 | 31.4 |
| 45 min | 88.4 | 83.2 |
| 60 min | 89.8 | 90.1 |

The enteric resistance followed by rapid drug release behaviour was retained in USP pH 4.1-5.5 buffer.
Tablet was intact in SGF and disintegration was observed within 7 and 10 minutes for 5 mg/cm² and 6 mg/cm² coating levels respectively in SIF

Example 4

Sodium Alginate (40-90 cP in 1% Aqueous Solution)

Coating of 16 mg/cm$^2$ polymer (HPMC 4 mg/cm$^2$+sodium alginate 12 mg/cm$^2$)
Formula for Polymer Coating Suspension on 300 g Tablets.

| Ingredient | Manufacturer | Quantity/Batch [g] | Solid content [g] |
|---|---|---|---|
| MANUCOL ® DH | FMC Biopolymers | 45 | 45 |
| HPMC(6 cP) | Shinetsu | 15 | 15 |
| Talc | Luznac | 7.5 | 7.5 |
| PEG 6000 (10% w.r.t HPMC) | Laffans Petrochemicals | 1.5 | 1.5 |
| Yellow iron oxide | BASF | 0.075 | 0.075 |
| Purified Water | | 1656.88 | |
| Total | | 1726.88 | 69.075 |

Procedure for Coating Suspension Preparation:
Sodium Alginate was weighed and kept under stirring with water for 2 hours on an overhead stirrer to prepare 5% solution.
Weighed quantity of HPMC was added to 135 g of water and stirred for 60 minutes using an overhead stirrer.
PEG 6000 was dissolved in 15 g of hot water (70-75° C.) and added to step 2
Talc and colour were homogenized with remaining amount of water for 30 minutes.
Suspension of step 2 was added to solution of step 1
Homogenized talc suspension was added to Alginate solution and stirring was continued for further 30 mins.
The final prepared suspension was passed through a sieve of 300 microns (60#).
This suspension was further sprayed onto tablets in a coating pan.
Coating:
Coating done upto 16 mg/cm$^2$ coating level
Suspension applied: 1223 g
Curing parameter: 24 hrs at 60° C. in a tray dryer.
Results:
  Appearance—Yellow coloured tablets with smooth surface
  Enteric protection was achieved with 4% drug release in 0.1N HCl 36%, 88% and 92% drug release was observed in 30, 45 minutes and 60 minutes respectively in USP pH 6.8 buffer with 16 mg/cm$^2$ coating level.
  Resistance to alcohol dose dumping was also observed with 16 mg/cm$^2$ coating level at 5%, 10%, 20% and 40% alcohol

| | Release [%] after 2 hr. in alcoholic HCl-HPMC:Na-Alginate(1:3) | |
|---|---|---|
| Coating 16 mg/cm$^2$ | 5% Alcoholic HCl 4% | 10% Alcoholic HCl 4% |
| | 20% Alcoholic HCl 3% | 40% Alcoholic HCl 3% |

The enteric resistance followed by rapid drug release behaviour was retained in USP pH 4.5-5.5 buffer.
Tablet was intact in SGF and disintegration was observed within 30 minutes in SIF.

Example 5

Sodium Alginate (40-90 cP in 1% Aqueous Solution)

Coating of 16 mg/cm$^2$ polymer (EUDRAGIT® NM 30D 2.7 mg/cm$^2$+sodium alginate 13.3 mg/cm$^2$)
Formula for Polymer Coating Suspension on 300 g Tablets.

| Ingredient | Manufacturer | Quantity/Batch [g] | Solid content [g] |
|---|---|---|---|
| MANUCOL ® DH (5% solution in water) | FMC Biopolymers | 1500.0 | 75.0 |
| EUDRAGIT ® NM 30D | Evonik industries | 50.0 | 15.0 |
| Talc | Luznac | 7.5 | 7.5 |
| Yellow iron oxide | BASF | 0.1 | 0.1 |
| Purified Water | | 882.0 | |
| Total | | 2439.6 | 67.6 |

Procedure for Coating Suspension Preparation:
  Sodium Alginate was weighed and kept under stirring with water for 30 minutes on an overhead stirrer to prepare 5% solution.
  pH of sodium alginate was raised to 10 by addition of 50 ml of 0.1 N NaOH.
  Talc and colour were homogenized with remaining amount of water for 30 minutes.
  Homogenized talc suspension and EUDRAGIT® NM 30D were added to Alginate solution of step 2 and stirring was continued for further 30 mins.
  The final prepared suspension was passed through a sieve of 300 microns (60#).
  This suspension was further sprayed onto tablets in a coating pan.
Coating:
Coating done up to 16 mg/cm$^2$ coating level
Suspension applied: 1151.94 g
Curing parameter: 24 hrs at 60° C. in a tray dryer.
Results:
  Appearance—Yellow coloured tablets with smooth surface
  Enteric protection was achieved with 4.3% drug release in 0.1N HCl 5.3%, 85% and 90% drug release was observed in 30, 45 minutes and 60 minutes respectively in USP pH 6.8 buffer with 16 mg/cm$^2$ coating level.
  Resistance to alcohol dose dumping was also observed with 16 mg/cm$^2$ coating level at 5%, 10%, 20% and 40% alcohol

| | Release [%] after 2 hr. in alcoholic HCl-EUDRAGIT ® NM 30 D d.s.:Na-Alginate (1:5) | |
|---|---|---|
| Coating 16 mg/cm$^2$ | 5% Alcoholic HCl 4% | 10% Alcoholic HCl 4% |
| | 20% Alcoholic HCl 3% | 40% Alcoholic HCl 2% |

The enteric resistance followed by rapid drug release behaviour was retained in USP pH 5.5 buffer.
Tablet was intact in SGF and disintegration was observed within 20 minutes in SIF

Example 6

Sodium Alginate (40-90 cP in 1% Aqueous Solution)

Coating of 16 mg/cm² polymer (EUDRAGIT® NM 30D 3.2 mg/cm²+sodium alginate 12.8 mg/cm²
Formula for Polymer Coating Suspension on 300 g Tablets.

| Ingredient | Manufacturer | Quantity/Batch [g] | Solid content [g] |
|---|---|---|---|
| MANUCOL® DH (5% solution in water) | FMC Biopolymers | 1200.0 | 60.0 |
| EUDRAGIT® NM 30D | Evonik industries | 50.0 | 15.0 |
| Talc | Luznac | 7.5 | 7.5 |
| Yellow iron oxide | BASF | 0.1 | 0.1 |
| Purified Water | | 1257.4 | |
| Total | | 2064.0 | 67.6 |

Procedure for Coating Suspension Preparation:
  Sodium Alginate was weighed and kept under stirring with water for 30 minutes on an overhead stirrer to prepare 5% solution.
  pH of sodium alginate was raised to 10 by addition of 50 ml of 0.1 N NaOH.
  Talc and colour were homogenized with remaining amount of water for 30 minutes.
  Homogenized talc suspension and EUDRAGIT® NM 30D were added to Alginate solution of step 2 and stirring was continued for further 30 mins.
  The final prepared suspension was passed through a sieve of 300 microns (60#).
  This suspension was further sprayed onto tablets in a coating pan.

Coating:
Coating done upto 16 mg/cm² coating level
Suspension applied: 1187.55 g
Curing parameter: 24 hrs at 60° C. in a tray dryer.
  Results:
  Appearance—Yellow coloured tablets with smooth surface
  Enteric protection was achieved with 5.8% drug release in 0.1N HCl 44.6%, 89.7% and 93.8 drug release was observed in 30, 45 minutes and 60 minutes respectively in USP pH 6.8 buffer with 16 mg/cm² coating level.
  Resistance to alcohol dose dumping was also observed with 16 mg/cm² coating level at 5%, 10%, 20% and 40% alcohol

| | Release [%] after 2 hr in alcoholic HCl.- EUDRAGIT® NM 30 D d.s.:Na Alginate (1:4) | |
|---|---|---|
| Coating 16 mg/cm² | 5% Alcoholic HCl 0% | 10% Alcoholic HCl 0% |
| | 20% Alcoholic HCl 1% | 40% Alcoholic HCl 1% |

The enteric resistance followed by rapid drug release behavior was retained in USP pH 5.5 buffer. Tablet was intact in SGF and disintegration was observed within 17 minutes in SIF

Example 7

Sodium Alginate (40-90 cP in 1% Aqueous Solution)

Coating of 16 mg/cm² polymer (EUDRAGIT® NM 30D 4 mg/cm²+sodium alginate 12 mg/cm²)
Formula for Polymer Coating Suspension on 300 g Tablets.

| Ingredient | Manufacturer | Quantity/Batch [g] | Solid content [g] |
|---|---|---|---|
| MANUCOL® DH (5% solution in water) | FMC Biopolymers | 900 | 45 |
| EUDRAGIT® NM 30D | Evonik industries | 50 | 15 |
| Talc | Luznac | 7.5 | 7.5 |
| Yellow iron oxide | BASF | 0.075 | 0.075 |
| Purified Water | | 731.92 | |
| Total | | 1689.5 | 67.58 |

Procedure for Coating Suspension Preparation:
  Sodium Alginate was weighed and kept under stirring with water for 30 minutes on an overhead stirrer to prepare 5% solution.
  pH of sodium alginate was raised to 10 by addition of 25 ml of 0.1 N NaOH.
  Talc and colour were homogenized with remaining amount of water for 30 minutes.
  Homogenized talc suspension and EUDRAGIT® NM 30D were added to Alginate solution of step 2 and stirring was continued for further 30 mins.
  The final prepared suspension was passed through a sieve of 300 microns (60#).
  This suspension was further sprayed onto tablets in a coating pan.

Coating:
Suspension applied: 1196 g
Curing parameter: 24 hrs at 60° C. in a tray dryer.
Results:
  Appearance—Yellow coloured tablets with smooth surface
  Enteric protection was achieved with 4.2% drug release in 0.1N HCl 73.7%, 92.9% and 94.5 drug release was observed in 30, 45 minutes and 60 minutes respectively in USP pH 6.8 buffer with 16 mg/cm² coating level.
  Resistance to alcohol dose dumping was also observed with 16 mg/cm² coating level at 5%, 10%, 20% and 40% alcohol

| | Release [%] after 2 hr in alcoholic HCl- EUDRAGIT® NM 30 D d.s.:Na Alginate (1:3) | |
|---|---|---|
| Coating 16 mg/cm² | 5% Alcoholic HCl 4% | 10% Alcoholic HCl 4% |
| | 20% Alcoholic HCl 3% | 40% Alcoholic HCl 2% |
| Coating 16 mg/cm² | Release [%] after 2 hr in alcoholic HCl followed by buffer pH 6.8 | |

-continued

| Time | 5% Alcoholic HCl followed by buffer pH 6.8 | 10% Alcoholic HCl followed by buffer pH 6.8 |
|---|---|---|
| 30 min | 44.8 | 12.3 |
| 45 min | 91.0 | 65.4 |
| 60 min | 93.7 | 94.8 |

| Time | 20% Alcoholic HCl followed by buffer pH 6.8 | 40% Alcoholic HCl followed by buffer pH 6.8 |
|---|---|---|
| 30 min | 17.8 | 31.2 |
| 45 min | 91.1 | 84.8 |
| 60 min | 94.3 | 91.2 |

The enteric resistance followed by rapid drug release behavior was retained in USP pH 5.5 buffer.

Tablet was intact in SGF and disintegration was observed within 36 minutes in SIF

Example 8

Sodium Alginate (40-90 cP in 1% Aqueous Solution)

Coating of 16 mg/cm$^2$ polymer (EUDRAGIT® NE 30 D 4 mg/cm$^2$+sodium alginate 12 mg/cm$^2$)
Formula for Polymer Coating on 300 g Tablets.

| Ingredient | Manufacturer | Quantity/Batch [g] | Solid content [g] |
|---|---|---|---|
| MANUCOL® DH (5% solution in water) | FMC Biopolymers | 900 | 45 |
| EUDRAGIT® NE 30D | Evonik industries | 50 | 15 |
| Talc | Luznac | 7.5 | 7.5 |
| Yellow iron oxide | BASF | 0.075 | 0.075 |
| Purified Water | | 731.92 | |
| Total | | 1689.5 | 67.58 |

Procedure for Coating Suspension Preparation:
  Sodium Alginate was weighed and kept under stirring with water for 30 minutes on an overhead stirrer to prepare 5% solution.
  pH of sodium alginate was raised to 10 by addition of 25 ml of 0.1 N NaOH.
  Talc and colour were homogenized with remaining amount of water for 30 minutes.
  Homogenized talc suspension and EUDRAGIT® NM 30D were added to Alginate solution of step 2 and stirring was continued for further 30 mins.
  The final prepared suspension was passed through a sieve of 300 microns (60#).
  This suspension was further sprayed onto tablets in a coating pan.
Coating:
Suspension applied: 1196 g
Curing parameter: 24 hrs at 60° C. in a tray dryer.
Results:
  Appearance—Yellow coloured tablets with smooth surface
  Enteric protection was achieved with 5% drug release in 0.1N HCl
  7%, 81% and 89% drug release was observed in 30, 45 minutes and 60 minutes respectively in USP pH 6.8 buffer with 16 mg/cm$^2$ coating level.

Resistance to alcohol dose dumping was also observed with 16 mg/cm$^2$ coating level at 5%, 10%, 20% and 40% alcohol

| Release [%] after 2 hr in alcoholic HCl-EUDRAGIT® NE 30 D d.S.:Na Alginate (1:3) | | |
|---|---|---|
| Coating 16 mg/cm" | 5% Alcoholic HCl 4% | 10% Alcoholic HCl 4% |
| | 20% Alcoholic HCl 2.9% | 40% Alcoholic HCl 2% |

The enteric resistance followed by rapid drug release behaviour was retained in USP pH 5.5 buffer.
Tablet was intact in SGF and disintegration was observed within 25 minutes in SIF.

Example 9

Sodium Alginate (40-90 cP in 1% Aqueous Solution)

Coating of 16 mg/cm$^2$ polymer (Kollicoat® SR 30 D 4 mg/cm$^2$+sodium alginate 12 mg/cm$^2$)
Formula for Polymer Coating on 300 g Tablets.

| Ingredient | Manufacturer | Quantity/Batch [g] | Solid content [g] |
|---|---|---|---|
| MANUCOL® DH (4% solution in water) | FMC Biopolymers | 1125 | 45 |
| Kollicoat® SR 30 D | BASF | 50 | 15 |
| Talc (12% w.r.t Kollicoat® SR 30D) | Luznac | 1.8 | 1.8 |
| Yellow iron oxide | BASF | 0.075 | 0.075 |
| Propylene glycol (3% w.r.t Kollicoat® SR 30D) | Loba chemie | 0.45 | 0.45 |
| Purified Water | | 900.18 | |
| Total | | 2077.5 | 67.58 |

Procedure for Coating Suspension Preparation:
  Sodium Alginate was weighed and kept under stirring with water for 2 hours on an overhead stirrer to prepare 5% solution.
  Talc and colour were homogenized with remaining amount of water for 30 minutes.
  Propylene glycol was added to Kollicoat® SR 30 D and mixed for 30 minutes on an magnetic stirrer.
  Suspension of step 3 was added to solution of step 1
  Homogenized talc suspension was added to Alginate solution and stirring was continued for further 30 mins.
  The final prepared suspension was passed through a sieve of 300 microns (60#).
  This suspension was further sprayed onto tablets in a coating pan.
Coating:
Coating done upto 16 mg/cm$^2$ coating level
Suspension applied: 1470 g
Curing parameter: 24 hrs at 60° C. in a tray dryer.
Results:
  Appearance—Yellow coloured tablets with smooth surface
  Enteric protection was achieved with 5% drug release in 0.1N HCl
  82%, 89% and 91% drug release was observed in 30, 45 minutes and 60 minutes respectively in USP pH 6.8 buffer with 16 mg/cm$^2$ coating level.

Resistance to alcohol dose dumping was also observed with 16 mg/cm² coating level at 5%, 10%, 20% and 40% alcohol

| | Release [%] after 2 hr. in alcoholic HCl-Kollicoat ® SR 30 D d.s.:Na Alginate (1:3) | |
|---|---|---|
| Coating 16 mg/cm² | 5% Alcoholic HCl 5% | 10% Alcoholic HCl 5% |
| | 20% Alcoholic HCl 5% | 40% Alcoholic HCl 3% |

The enteric resistance followed by rapid drug release behaviour was retained in USP pH 5.5 buffer.
Tablet was intact in SGF and disintegration was observed within 20 minutes in SIF.

Example 10

Sodium Alginate (40-90 cP in 1% Aqueous Solution)

Coating of 16 mg/cm² polymer (EUDRAGIT® RS 30 D 4 mg/cm²+sodium alginate 12 mg/cm²)
Formula for Polymer Coating Suspension on 300 g Tablets.

| Ingredient | Manufacturer | Quantity/Batch [g] | Solid content [g] |
|---|---|---|---|
| MANUCOL ® DH (5% solution in water) | FMC Biopolymers | 900 | 45 |
| EUDRAGIT ® RS 30D | Evonik industries | 50 | 15 |
| Talc | Luznac | 7.5 | 7.5 |
| Yellow iron oxide | BASF | 0.075 | 0.075 |
| Purified Water | | 732 | |
| Total | | 1689.5 | 67.58 |

Procedure for Coating Suspension Preparation:
  Sodium Alginate was weighed and kept under stirring with water for 2 hours on an overhead stirrer to prepare 5% solution.
  Talc and colour were homogenized with remaining amount of water for 30 minutes.
  Homogenized talc suspension and EUDRAGIT® RS 30 D were added to Alginate solution and stirring was continued for further 30 mins.
  The final prepared suspension was passed through a sieve of 300 microns (60#).
  This suspension was further sprayed onto tablets in a coating pan.
Coating:
Coating done up to 16 mg/cm² coating level
Suspension applied: 1470 g
Curing parameter: 24 hrs at 60° C. in a tray dryer.
Results:
  Appearance: Yellow coloured tablets with smooth surface
  Enteric protection was achieved with 4% drug release in 0.1N HCl
  7%, 84% and 91% drug release was observed in 30, 45 minutes and 60 minutes respectively in USP pH 6.8 buffer with 16 mg/cm² coating level.
  Resistance to alcohol dose dumping was also observed with 16 mg/cm² coating level at 5%, 10%, 20% and 40% alcohol.

| | Release [%] after 2 hr. in alcoholic HCl-EUDRAGIT ® RS 30 D d.S.:Na Alginate (1:3) | |
|---|---|---|
| Coating 16 mg/cm² | 5% Alcoholic HCl 4% | 10% Alcoholic HCl 3% |
| | 20% Alcoholic HCl 2% | 40% Alcoholic HCl 1% |

The enteric resistance followed by rapid drug release behaviour was retained in USP pH 5.5 buffer.
Tablet was intact in SGF and disintegration was observed within 25 minutes in SIF.

Example 11

Sodium Alginate (40-90 cP in 1% Aqueous Solution) Pellet Formulation

EUDRAGIT® NM 30D: MANUCOL® DH: 1:3 coating
Formula for Polymer Coating Suspension on 600 g Lansoprazole Pellets (Size 1-1.4 mm, 11.7-14.3% w/w Drug Loading)

| Ingredient | Manufacturer | Quantity/Batch [g] | Solid content [g] |
|---|---|---|---|
| MANUCOL ® DH (5% solution in water) | FMC Biopolymers | 4500 | 225 |
| EUDRAGIT ® NM 30D | Evonik industries | 250 | 75 |
| Talc | Luznac | 37.5 | 37.5 |
| Purified Water | | 1962.5 | |
| Total | | 6750 | 337.5 |

Procedure for Coating Suspension Preparation:
  Sodium Alginate was weighed and kept under stirring with water for 30 minutes on an overhead stirrer to prepare 5% solution.
  pH of sodium alginate was raised to 10 by addition of 90 ml of 0.1 N NaOH.
  Talc and colour were homogenized with remaining amount of water for 30 minutes.
  Homogenized talc suspension and EUDRAGIT® NM 30D were added to Alginate solution of step 2 and stirring was continued for further 30 mins.
  The final prepared suspension was passed through a sieve of 300 microns (60#).
  This suspension was further sprayed onto pellets in FBP (GPCG 3.1)
Coating:
Coating done up to 50% polymer level
Suspension applied: 6750 g
Curing parameter: Fluidisation for 2 hours at 50° C.
Results:
  Appearance—Cream coloured pellets
  Enteric protection was not achieved with 17.5% and 10.1% drug release in 0.1N HCl after 60 minutes with 40% and 45% polymer coating levels.
  Enteric protection was achieved with 8.9% drug release in 0.1N HCl after 60 minutes for 50% w/w polymer coating level
  71.6% drug release was observed in 60 minutes respectively in USP pH 6.8 buffer with 50% w/w polymer coating level
  Resistance to alcohol dose dumping was observed with 50% w/w polymer coating level at 5%, 10%, 20% and 40% alcohol (ethanol) levels.

| Coating 50% polymer | Release [%] after 2 hr. in alcoholic HCl-EUDRAGIT ® NM 30D | |
|---|---|---|
| | 5% Alco HCl 3% | 10% Alco HCl 0.4% |
| | 20% Alco HCl 0.2% | 40% Alco HCl 0% |

Enteric resistance followed by 89% drug release was observed in 60 minutes in USP pH 5.5 buffer with 50% polymer coating level Example 12

Sodium Alginate (not Less than 45 cP in 1% Aqueous Solution)

Coating of 4 mg/cm$^2$ polymer plain alginate
Formula for Sodium Alginate (Food Grade) Coating on 300 g Tablets.

| Ingredient | Manufacturer | Quantity/Batch [g] | Solid content [g] |
|---|---|---|---|
| Sodium alginate (Food grade) (5% solution in water) | Loba chemie | 300 | 15 |
| Talc | Luznac | 7.5 | 7.5 |
| Yellow iron oxide | BASF | 0.08 | 0.08 |
| Purified Water | | 256.8 | |
| Total | | 564.38 | 22.58 |

Procedure for Coating Suspension Preparation:
  Sodium Alginate was weighed and kept under stirring with water for 1 hour on an overhead stirrer to prepare 10% solution.
  Talc and colour were homogenized with remaining amount of water for 30 minutes.
  Homogenized talc suspension was added to Alginate solution and stirring was continued for further 30 mins.
  The final prepared suspension was passed through a sieve of 300 microns (60#).
  This suspension was further sprayed onto tablets in a coating pan
Coating:
Suspension applied for 3 mg/cm$^2$ coating level: 300 g
Suspension applied for 4 mg/cm$^2$ coating level: 400 g
Results:
  Appearance: Yellow coloured tablets with smooth surface
  Enteric protection was achieved with 8.2% drug release in 0.1N HCl with 3 mg/cm$^2$ coating level.
  88.9%, 91.6% and 92.2% drug release was observed in 30, 45 minutes and 60 minutes respectively in USP pH 6.8 buffer with 3 mg/cm$^2$ coating level.
  Enteric protection was achieved with 7.0% drug release in 0.1N HCl with 4 mg/cm$^2$ coating level.
  86.2%, 87.8% and 88.7% drug release was observed in 30, 45 minutes and 60 minutes respectively in USP pH 6.8 buffer with 4 mg/cm$^2$ coating level.
  Resistance to alcohol dose dumping was not observed with 3 mg/cm$^2$ at 5% and 20% alcohol but alcohol resistance was observed at 10% and 40% alcohol
  Resistance to alcohol dose dumping was observed with 4 mg/cm$^2$ coating level at 5%, 10%, 20% and 40% alcohol

| Coating | Release [%] after 2 hr. in alcoholic HCl-Plain Na Alginate | |
|---|---|---|
| | 5% Alco HCl | 10% Alco HCl |
| 3 mg/cm$^2$ | 57% | 6% |
| 4 mg/cm$^2$ | 9% | 6% |
| Coating | 20% Alco HCl | 40% Alco HCl |
| 3 mg/cm$^2$ | 10% | 6.5% |
| 4 mg/cm$^2$ | 5% | 5% |

3 mg/cm$^2$ coated tablet was intact in SGF and disintegration was observed within 18 minutes in SIF
4 mg/cm$^2$ coated tablet was intact in SGF and disintegration was observed within 20 minutes in SIF Example 13

Sodium Alginate (not Less than 45 cP in 1% Aqueous Solution)

Coating of 6 mg/cm$^2$ polymer (EUDRAGIT® NM 30D 4 mg/cm$^2$+sodium alginate 2 mg/cm$^2$)
Formula for Polymer Coating Suspension on 300 g Tablets.

| Ingredient | Manufacturer | Quantity/Batch [g] | Solid content [g] |
|---|---|---|---|
| Sodium alginate (Food grade) | Loba chemie | 15 | 15 |
| EUDRAGIT ® NM 30 D | Evonik industries | 100 | 30 |
| Talc | Luznac | 9 | 9 |
| Yellow iron oxide | BASF | 0.15 | 0.15 |
| Purified Water | | 552.73 | |
| Total | | 676.87 | 54.15 |

Procedure for Coating Suspension Preparation:
Sodium Alginate was weighed and kept under stirring with water for 1 hour on an overhead stirrer to prepare 10% solution.
Talc and colour were homogenized with remaining amount of water for 30 minutes.
Homogenized talc suspension and EUDRAGIT® NM 30D were added to Alginate solution and stirring was continued for further 30 mins.
The final prepared suspension was passed through a sieve of 300 microns (60#).
This suspension was further sprayed onto tablets in a coating pan
Coating
Suspension applied: 239.6 g
Curing: 24 h at 60° C. in a tray dryer
Results:
  Appearance—Yellow coloured tablets with smooth surface
  Enteric protection was achieved with 3.8% drug release in 0.1N HCl
  11.8%, 30.5% and 67% drug release was observed in 30, 45 minutes and 60 minutes respectively in USP pH 6.8 buffer with 6 mg/cm$^2$ coating level.
  Resistance to alcohol dose dumping was also observed with 6 mg/cm$^2$ coating level at 5%, 10%, 20% and 40% alcohol

| Release [%] after 2 hr. in alcoholic HCl-EUDRAGIT ® NM 30 D d.s.:Na Alginate (1:0.5) | | |
|---|---|---|
| Coating 6 mg/cm² | 5% Alcoholic HCl 3% | 10% Alcoholic HCl 3% |
| | 20% Alcoholic HCl 2% | 40% Alcoholic HCl 3% |

Tablet was intact after disintegration test in SGF and swelling was observed within 60 minutes in SIF

Example 14C (Comparative)

Potassium Alginate (200-400 cP for 1% Aqueous Solution)

Coating of 2 mg/cm² Potassium Alginate
Formula for Polymer Coating Suspension on 300 g Tablets.

| Ingredient | Manufacturer | Quantity/Batch [g] | Solid content [g] |
|---|---|---|---|
| Potassium Alginate (PROTANAL KF200 FTS) | FMC Biopolymers | 500 | 15 |
| Talc | Luznac | 7.5 | 7.5 |
| Yellow iron oxide | BASF | 0.075 | 0.075 |
| Purified Water | | 621.42 | |
| Total | | 1129 | 22.58 |

Procedure for Coating Suspension Preparation:
  Potassium Alginate was weighed and kept under stirring with water for 2 hours on an overhead stirrer to prepare 3% solution.
  Talc and colour were homogenized with remaining amount of water for 30 minutes.
  Homogenized talc suspension was added to Potassium alginate solution of step 2 and stirring was continued for further 30 mins.
  The final prepared suspension was passed through a sieve of 300 microns (60#).
  This suspension was further sprayed onto tablets in a coating pan.
Coating:
Suspension applied for 2 mg/cm²: 199.22 g
Curing parameter: No curing
Results:
  Appearance—Yellow coloured tablets with smooth surface
  Enteric protection was not achieved with 34.5% drug release in 0.1N HCl for 2 mg/cm² coating level.

Example 15

Sodium Alginate (50-150 cP in 1% Aqueous Solution)

Coating of 4 mg/cm² polymer pure sodium alginate
Formula for Coating Suspension on 300 g Tablets

| Ingredient | Manufacturer | Quantity/Batch [g] | Solid content [g] |
|---|---|---|---|
| KELTONE ® LVCR (5% solution in water) | FMC Biopolymers | 250 | 15 |
| Talc | Luznac | 7.5 | 7.5 |
| Yellow iron oxide | BASF | 0.075 | 0.075 |
| Purified Water | | 194.02 | |
| Total | | 451.6 | 22.58 |

Procedure for Coating Suspension Preparation:
  Sodium Alginate was weighed and kept under stirring with water for 3 hours on an overhead stirrer to prepare 6% solution.
  Talc and colour were homogenized with remaining amount of water for 30 minutes.
  Homogenized talc suspension was added to Alginate solution and stirring was continued for further 30 mins.
  The final prepared suspension was passed through a sieve of 300 microns (60#).
  This suspension was further sprayed onto tablets in a coating pan.
Coating:
Suspension applied: 319.8 g
Curing parameter: No curing
Results:
  Appearance—Yellow coloured tablets with smooth surface
  Enteric protection was achieved with 7.7% drug release in 0.1N HCl
  Enteric protection was achieved with 65.1%, 82.6% and 88.2% drug release in 30, 45 and 60 minutes respectively in USP pH 6.8 buffer with 4 mg/cm² coating level.
  Resistance to alcohol dose dumping was also observed with 4 mg/cm² coating level at 5%, 10%, 20% and 40% alcohol levels.

| Release [%] after 2 hr. in alcoholic HCl-Plain Na Alginate | | |
|---|---|---|
| Coating 4 mg/cm² | 5% Alco HCl 15% | 10% Alco HCl 10% |
| | 20% Alco HCl 6% | 40% Alco HCl 7% |

The enteric resistance followed by rapid drug release behaviour was retained in USP pH 5.5 buffer.
Tablet was intact in SGF and disintegration was observed within 15 minutes in SIF

Example 16

Sodium Alginate (50-150 cP in 1% Aqueous Solution)

Coating of 16 mg/cm² polymer (EUDRAGIT® NM 30D 4 mg/cm²+sodium alginate 12 mg/cm²)
Formula for Polymer Coating Suspension on 300 g Tablets.

| Ingredient | Manufacturer | Quantity/Batch [g] | Solid content [g] |
|---|---|---|---|
| KELTONE ® LVCR (5% solution in water) | FMC Biopolymers | 900 | 45 |

-continued

| Ingredient | Manufacturer | Quantity/ Batch [g] | Solid content [g] |
|---|---|---|---|
| EUDRAGIT ® NM 30 D | Evonik industries | 50 | 15 |
| Talc | Luznac | 7.5 | 7.5 |
| Yellow iron oxide | BASF | 0.075 | 0.075 |
| Purified Water | | 731.92 | |
| Total | | 1689.5 | 67.58 |

Procedure for Coating Suspension Preparation:
  Sodium Alginate was weighed and kept under stirring with water for 2 hours on an overhead stirrer to prepare 5% solution.
  Talc and colour were homogenized with remaining amount of water for 30 minutes.
  Homogenized talc suspension and EUDRAGIT® NM 30D 30D were added to Alginate solution and stirring was continued for further 30 mins.
  The final prepared suspension was passed through a sieve of 300 microns (60#).
  This suspension was further sprayed onto tablets in a coating pan.
Coating:
Suspension applied: 1196 g
Curing parameter: 24 hrs at 60° C. in a tray dryer.
Results:
  Appearance—Yellow coloured tablets with smooth surface
  Enteric protection was achieved with 4% drug release in 0.1N HCl
  20.6%, 85.8% and 92.0 drug release was observed in 30, 45 minutes and 60 minutes respectively in USP pH 6.8 buffer with 16 mg/cm$^2$ coating level.
  Resistance to alcohol dose dumping was also observed with 16 mg/cm$^2$ coating level at 5%, 10%, 20% and 40% alcohol

| Release [%] after 2 hr. in alcoholic HCl- EUDRAGIT ® NM 30 D d.s.:Na Alginate(1:3) | | |
|---|---|---|
| Coating 16 mg/cm$^2$ | 5% Alcoholic HCl 4% | 10% Alcoholiv HCl 4% |
| | 20% Alcoholic HCl 2% | 40% Alcoholic HCl 1% |

The enteric resistance followed by rapid drug release behaviour was retained in USP pH 5.5 buffer.
Tablet was intact in SGF and disintegration was observed within 25 minutes in SIF

Example 17

Sodium Alginate (70-200 cP in 1% Aqueous Solution)

Coating of 4 mg/cm$^2$ polymer plain sodium alginate)
Formula for Coating Suspension on 300 g Tablets

| Ingredient | Manufacturer | Quantity/ Batch [g] | Solid content [g] |
|---|---|---|---|
| PROTANAL ® LF 240 D (6% solution in water) | FMC Biopolymers | 250 | 15 |
| Talc | Luznac | 7.5 | 7.5 |
| Yellow iron oxide | BASF | 0.075 | 0.075 |
| Purified Water | | 306.92 | — |
| Total | | 564.5 | 22.58 |

Procedure for Coating Suspension Preparation:
  Sodium Alginate was weighed and kept under stirring with water for 30 minutes on an overhead stirrer to prepare 6% solution.
  Talc and colour were homogenized with remaining amount of water for 30 minutes.
  Homogenized talc suspension was added to Alginate solution of step 2 and stirring was continued for further 30 mins.
  The final prepared suspension was passed through a sieve of 300 microns (60#).
  This suspension was further sprayed onto tablets in a coating pan.
Coating:
Coating done up to 4 mg/cm$^2$ coating level
Suspension applied: 399.75 g
Curing parameter: No curing
Results:
  Appearance—Yellow coloured tablets with smooth surface
  Enteric protection was achieved with 6.6% drug release in 0.1N HCl
  59.5%, 86.8% and 91% drug release was observed in 30, 45 and 60 minutes respectively in USP pH 6.8 buffer with 4 mg/cm$^2$ coating level.
  Resistance to alcohol dose dumping was also observed with 4 mg/cm$^2$ coating level at 5%, 10%, 20% and 40% alcohol levels

| Release [%] after 2 hr. in alcoholic HCl-Plain Na Alginate | | |
|---|---|---|
| Coating 4 mg/cm$^2$ | 5% Alcoholic HCl 6% | 10% Alcoholic HCl 7% |
| | 20% Alcoholic HCl 6% | 40% Alcoholic HCl 6% |

The enteric resistance followed by rapid drug release was retained in USP pH 5.5 buffer.
Tablet was intact in SGF and disintegration was observed within 25 minutes in SIF

Example 18C (Comparative)

Sodium Alginate (70-200 cP in 1% Aqueous Solution)

Coating of 3 mg/cm² polymer plain sodium alginate)
Formula for Coating Suspension on 300 g Tablets

| Ingredient | Manufacturer | Quantity/Batch [g] | Solid content [g] |
|---|---|---|---|
| PROTANAL ® LF 240 D (6% solution in water) | FMC Biopolymers | 250 | 15 |
| Talc | Luznac | 7.5 | 7.5 |
| Yellow iron oxide | BASF | 0.075 | 0.075 |
| Purified Water | | 306.92 | — |
| Total | | 564.5 | 22.58 |

Procedure for Coating Suspension Preparation:
  Sodium Alginate was weighed and kept under stirring with water for 30 minutes on an overhead stirrer to prepare 6% solution.
  Talc and colour were homogenized with remaining amount of water for 30 minutes.
  Homogenized talc suspension was added to Alginate solution of step 2 and stirring was continued for further 30 mins.
  The final prepared suspension was passed through a sieve of 300 microns (60#).
  This suspension was further sprayed onto tablets in a coating pan.
Coating:
Coating done up to 3 mg/cm² coating level
Suspension applied: 300 g
Curing parameter: No curing
Results:
  Appearance—Yellow coloured tablets with smooth surface
  Enteric protection was not achieved with 25% drug release in 0.1N HCl

Example 19

Sodium Alginate (70-200 cP in 1% Aqueous Solution)

Coating of 16 mg/cm² polymer (EUDRAGIT® NM 30D 4 mg/cm²+sodium alginate 12 mg/cm²)
Formula for 20% w/w Polymer Coating Suspension on 300 g Tablets.

| Ingredient | Manufacturer | Quantity/Batch [g] | Solid content [g] |
|---|---|---|---|
| PROTANAL ® LF 240 D (5% solution in water) | FMC Biopolymers | 900 | 45 |
| EUDRAGIT ® NM 30D | Evonik industries | 50 | 15 |
| Talc | Luznac | 7.5 | 7.5 |
| Yellow iron oxide | BASF | 0.075 | 0.075 |
| Purified Water | | 731.92 | |
| Total | | 1689.5 | 670575 |

Procedure for Coating Suspension Preparation:
  Sodium Alginate was weighed and kept under stirring with water for 2 hours on an overhead stirrer to prepare 5% solution.
  pH of sodium alginate was raised to 10 by addition of 30 ml of 0.1 N NaOH.
  Talc and colour were homogenized with remaining amount of water for 30 minutes.
  Homogenized talc suspension and EUDRAGIT® NM 30D were added to Alginate solution of step 2 and stirring was continued for further 30 mins.
  The final prepared suspension was passed through a sieve of 300 microns (60#).
  This suspension was further sprayed onto tablets in a coating pan.
Coating:
Suspension applied: 1196 g
Curing parameter: 24 hrs at 60° C. in a tray dryer.
Results:
  Appearance—Yellow coloured tablets with smooth surface
  Enteric protection was achieved with 4.1% drug release in 0.1N HCl
  66.2%, 92.5% and 94.0 drug release was observed in 30, 45 minutes and 60 minutes respectively in USP pH 6.8 buffer with 16 mg/cm² coating level.
  Resistance to alcohol dose dumping was also observed with 16 mg/cm² coating level at 5%, 10%, 20% and 40% alcohol

| | Release [%] after 2 hr. in alcoholic HCl-EUDRAGIT ® NM 30 D d.s.:Na Alginate(1:3) | |
|---|---|---|
| Coating 16 mg/cm² | 5% Alco HCl 3% | 10% Alco HCl 4% |
| | 20% Alco HCl 3% | 40% Alco HCl 1% |

The enteric resistance followed by rapid drug release behaviour was retained in USP pH 5.5 buffer.
  Tablet was intact in SGF and disintegration was observed within 25 minutes in SIF

Example 20

Potassium Alginate (200-400 cP for 1% Aqueous Solution)

Coating of 3 mg/cm² and 4 mg/cm² Potassium Alginate
Formula for Polymer Coating Suspension on 300 g Tablets.

| Ingredient | Manufacturer | Quantity/Batch [g] | Solid content [g] |
|---|---|---|---|
| Potassium Alginate (PROTANAL ® KF200 FTS) | FMC Biopolymers | 500 | 15 |
| Talc | Luznac | 7.5 | 7.5 |
| Yellow iron oxide | BASF | 0.075 | 0.075 |
| Purified Water | | 621.42 | |
| Total | | 1129 | 22.58 |

Procedure for Coating Suspension Preparation:
  Potassium Alginate was weighed and kept under stirring with water for 2 hours on an overhead stirrer to prepare 3% solution.

Talc and colour were homogenized with remaining amount of water for 30 minutes.

Homogenized talc suspension was added to Potassium alginate solution of step 2 and stirring was continued for further 30 mins.

The final prepared suspension was passed through a sieve of 300 microns (60#).

This suspension was further sprayed onto tablets in a coating pan.

Coating:
Suspension applied for 3 mg/cm$^2$: 677.4 g
Suspension applied for 4 mg/cm$^2$: 903.2 g
Curing parameter: No curing
Results:
  Appearance—Yellow coloured tablets with smooth surface
    Enteric protection was achieved with 13.1% drug release in 0.1N HCl. 85.0%, 91.3% and 92.9% drug release was observed in 30, 45 minutes and 60 minutes respectively in USP pH 6.8 buffer with 3 mg/cm$^2$ coating level.
  Enteric protection was achieved with 5.2% drug release in 0.1N HCl. 47.9%, 85.5% and 90.6% drug release was observed in 30, 45 minutes and 60 minutes respectively in USP pH 6.8 buffer with 4 mg/cm$^2$ coating level.
  Resistance to alcohol dose dumping was also observed with 3 mg/cm$^2$ and 4 mg/cm$^2$ coating level at 5%, 10%, 20% and 40% alcohol.

| | Release [%] after 2 hr. in alcoholic HCl- Plain potassium alginate | |
| --- | --- | --- |
| Coating | 5% Alco HCl | 10% Alco HCl |
| 3 mg/cm$^2$ | 6% | 6% |
| 4 mg/cm$^2$ | 5% | 5% |
| Coating | 20% Alco HCl | 40% Alco HCl |
| 3 mg/cm$^2$ | 7% | 4% |
| 4 mg/cm$^2$ | 3% | 2% |

The enteric resistance followed by rapid drug release behavior was retained in USP pH 5.1-5.5 buffer.
3 mg/cm$^2$ coated tablet was intact in SGF and disintegration was observed within 17 minutes in SIF
4 mg/cm$^2$ coated tablet was intact in SGF and disintegration was observed within 24 minutes in SIF Example 21

Potassium Alginate (200-400 cP for 1% Aqueous Solution)

Coating of 7 mg/cm$^2$ polymer (EUDRAGIT® NM 30D 1.75 mg/cm$^2$+potassium alginate 5.25 mg/cm$^2$)
Formula for Polymer Coating Suspension on 300 g Tablets

| Ingredient | Manufacturer | Quantity/Batch [g] | Solid content [g] |
| --- | --- | --- | --- |
| Potassium Alginate (PROTANAL KF FTS) | FMC Biopolymers | 750 | 22.5 |
| EUDRAGIT® NM 30D | Evonik industries | 25 | 7.5 |
| Talc | Luznac | 3.75 | 3.75 |
| Yellow iron oxide | BASF | 0.04 | 0.04 |
| Purified Water | | 910 | |
| Total | | 1689.39 | 33.79 |

Procedure for Coating Suspension Preparation:
  Potassium Alginate was weighed and kept under stirring with water for 2 hours on an overhead stirrer to prepare 3% solution.
  Talc and colour were homogenized with remaining amount of water for 30 minutes.
  Homogenized talc suspension and EUDRAGIT® NM 30D were added to Alginate solution of step 2 and stirring was continued for further 30 mins.
  The final prepared suspension was passed through a sieve of 300 microns (60#).
  This suspension was further sprayed onto tablets in a coating pan.
Coating:
Coating done up to 7 mg/cm$^2$ coating level
Suspension applied: 1047.21 g
Curing parameter: 60° C. for 24 hours in tray dryer
Results:
  Appearance—Yellow coloured tablets with smooth surface
  Enteric protection was achieved with 7.3% drug release in 0.1N HCl. 66%, 91.8% and 94.9% drug release was observed in 30, 45 minutes and 60 minutes respectively in USP pH 6.8 buffer with 4 mg/cm$^2$ coating level.
  Resistance to alcohol dose dumping was also observed with 7 mg/cm$^2$ coating level at 5%, 10%, 20% and 40% alcohol

| | Release [%] after 2 hr in alcoholic HCl-EUDRAGIT® NM 30 D d.s.:Potassium Alginate (1:3) | |
| --- | --- | --- |
| Coating 7 mg/cm$^2$ | 5% Alcoholic HCl 5% | 10% Alcoholic HCl 5% |
| | 20% Alcoholic HCl 4% | 40% Alcoholic HCl 3% |

The enteric resistance followed by rapid drug release behavior was retained in USP pH 5.1-5.5 buffer.
Tablet was intact in SGF and disintegration was observed within 15 minutes in SIF Example 22

Sodium Alginate (480-720 cP in 1% Aqueous Solution)

Coating of 6 mg/cm$^2$ plain sodium alginate
Formula for Coating Suspension Solution on 300 g Table

| Ingredient | Manufacturer | Quantity/Batch [g] | Solid content [g] |
| --- | --- | --- | --- |
| KELTONE® HVCR (3% solution in water) | FMC Biopolymers | 1000 | 30 |

-continued

| Ingredient | Manufacturer | Quantity/Batch [g] | Solid content [g] |
|---|---|---|---|
| Talc | Luznac | 7.5 | 7.5 |
| Yellow iron oxide | BASF | 0.075 | 0.075 |
| Purified Water | | 1242.84 | |
| Total | | 2258 | 67.58 |

Procedure for Coating Suspension Preparation:
  Sodium Alginate was weighed and kept under stirring with water for 3 hours on an overhead stirrer to prepare 6% solution.
  Talc and colour were homogenized with remaining amount of water for 30 minutes.
  Homogenized talc suspension was added to Alginate solution and stirring was continued for further 30 mins.
  The final prepared suspension was passed through a sieve of 300 microns (60#).
  This suspension was further sprayed onto tablets in a coating pan.
Coating:
Coating done up to 6 mg/cm$^2$ coating level
Suspension applied: 1199.25 g
Curing parameter: No curing
Results:
  Appearance—Yellow coloured tablets with smooth surface
  Enteric protection was achieved with 7.2% drug release in 0.1N HCl
  46.3%, 78.3% and 88.7% drug release was observed in 30, 45 and 60 minutes respectively in USP pH 6.8 buffer with 6 mg/cm$^2$ coating level.
  Resistance to alcohol dose dumping was also observed with 6 mg/cm$^2$ coating level at 10%, 20% and 40% alcohol levels.

| | Release [%] after 2 hr. in alcoholic HCl-Plain Na Alginate | |
|---|---|---|
| Coating 6 mg/cm$^2$ | 5% Alco HCl 7% | 10% Alco HCl 9% |
| | 20% Alco HCl 5% | 40% Alco HCl 4% |

Tablet was intact in SGF and disintegration was observed within 13 minutes in SIF Example 23

Sodium Alginate (480-720 cP in 1% Aqueous Solution)

Coating of 8 mg/cm$^2$ polymer pure sodium alginate
Formula for Coating Suspension on 300 g Tablets

| Ingredient | Manufacturer | Quantity/Batch [g] | Solid content [g] |
|---|---|---|---|
| KELTONE ® HVCR (3% solution in water) | FMC Biopolymers | 1000 | 30 |
| Talc | Luznac | 7.5 | 7.5 |
| Yellow iron oxide | BASF | 0.075 | 0.075 |
| Purified Water | | 1242.84 | |
| Total | | 2258 | 67.58 |

Procedure for Coating Suspension Preparation:
  Sodium Alginate was weighed and kept under stirring with water for 3 hours on an overhead stirrer to prepare 6% solution.
  Talc and colour were homogenized with remaining amount of water for 30 minutes.
  Homogenized talc suspension was added to Alginate solution and stirring was continued for further 30 mins.
  The final prepared suspension was passed through a sieve of 300 microns (60#).
  This suspension was further sprayed onto tablets in a coating pan.
Coating:
Coating done up to 8 mg/cm$^2$ coating level
Suspension applied: 1599 g
Curing parameter: No curing
Results:
  Appearance—Yellow coloured tablets with smooth surface
  Enteric protection was achieved with 5.7% drug release in 0.1N HCl
  35.3%, 89.5% and 93.9% drug release was observed in 30, 45 and 60 minutes respectively in USP pH 6.8 buffer with 8 mg/cm$^2$ coating level.
  Resistance to alcohol dose dumping was also observed with 8 mg/cm$^2$ coating level at 5%, 10%, 20% and 40% alcohol (ethanol) levels.

| | Release [%] after 2 hr. in alcoholic HCl-Plain Na Alginate | |
|---|---|---|
| Coating 8 mg/cm$^2$ | 5% Alcoholic HCl 5% | 10% Alcoholic HCl 5% |
| | 20% Alcoholic HCl 5% | 40% Alcoholic HCl 4% |

The enteric resistance followed by rapid drug release behaviour was retained in USP pH 5.5 buffer.
Tablet was intact in SGF and disintegration was observed within 20 minutes in SIF Example 24

Sodium Alginate (480-720 cP in 1% Aqueous Solution)

Coating of 12 mg/cm$^2$ polymer (EUDRAGIT® NM 30D 3 mg/cm$^2$+sodium alginate 9 mg/cm$^2$)
Formula for Polymer Coating Suspension on 300 g Tablets.

| Ingredient | Manufacturer | Quantity/Batch [g] | Solid content [g] |
|---|---|---|---|
| KELTONE ® HVCR (3% solution in water) | FMC Biopolymers | 1500 | 45 |
| EUDRAGIT ® NM 30D 30D | Evonik industries | 50 | 15 |

| Ingredient | Manufacturer | Quantity/ Batch [g] | Solid content [g] |
|---|---|---|---|
| Talc | Luznac | 7.5 | 7.5 |
| Yellow iron oxide | BASF | 0.075 | 0.075 |
| Purified Water | | 1821.42 | |
| Total | | 3379 | 67.58 |

Procedure for Coating Suspension Preparation:
  Sodium Alginate was weighed and kept under stirring with water for 2 hours on an overhead stirrer to prepare 3% solution.
  Talc and colour were homogenized with remaining amount of water for 30 minutes.
  Homogenized talc suspension and EUDRAGIT® NM 30D 30D were added to Alginate solution and stirring was continued for further 30 mins.
  The final prepared suspension was passed through a sieve of 300 microns (60#).
  This suspension was further sprayed onto tablets in a coating pan.
Coating:
Suspension applied: 1794.38 g
Curing parameter: 24 hrs at 60° C. in a tray dryer.
Results:
  Yellow coloured tablets with smooth surface
  Enteric protection was achieved with 4.5% drug release in 0.1N HCl
  5.3%, 86.9% and 94.9 drug release was observed in 30, 45 minutes and 60 minutes respectively in USP pH 6.8 buffer with 12 mg/cm² coating level.
  Resistance to alcohol dose dumping was also observed with 12 mg/cm² coating level at 10%, 20% and 40% alcohol levels.

| | Release [%] after 2 hr in alcoholic HCl-EUDRAGIT ® NM 30 D d.s.:sodium Alginate (1:3) | |
|---|---|---|
| Coating 12 mg/cm² | 5% Alcoholic HCl 5% | 10% Alcoholic HCl 5% |
| | 20% Alcoholic HCl 4% | 40% Alcoholic HCl 2% |

Tablet was intact in SGF and disintegration was observed within 20 minutes in SIF

Example 25C (Comparative)

Carrageenan

Coating of 10 mg/cm² Carrageenan
Formula for Coating Suspension on 300 g Tablets

| Ingredient | Manufacturer | Quantity/ Batch [g] | Solid content [g] |
|---|---|---|---|
| Carrageenan (Viscarin ® GP 109NF) (1.5% solution in water) | FMC Biopolymers | 2000 | 30 |
| Talc | Luznac | 15 | 15 |
| Yellow iron oxide | BASF | 0.15 | 0.15 |
| Purified Water | | 458 | |
| Total | | 2258 | 45.16 |

Procedure for Coating Suspension Preparation:
  Carrageenan was weighed and kept under stirring with water for 2 hours on an overhead stirrer to prepare 1.5% solution.
  Talc and colour were homogenized with remaining amount of water for 30 minutes.
  Homogenized talc suspension was added to Carrageenan solution of step 2 and stirring was continued for further 30 mins.
  The final prepared suspension was passed through a sieve of 300 microns (60#).
  This suspension was further sprayed onto tablets in a coating pan.
Coating:
Suspension applied: 2258 g
Curing parameter: No curing
Results:
  Yellow coloured tablets with smooth surface
  Enteric protection was not achieved with 92.7% drug release in 0.1N HCl for 10 mg/cm² coating level

Example 26C (Comparative)

Alginic Acid

Coating of 4 mg/cm² plain alginic acid
Formula for Coating Suspension on 300 g Tablets

| Ingredient | Manufacturer | Quantity/ Batch [g] | Solid content [g] |
|---|---|---|---|
| Alginic acid (6% solution in water) | FMC Biopolymers | 250 | 15 |
| Talc | Luznac | 7.5 | 7.5 |
| Yellow iron oxide | BASF | 0.075 | 0.075 |
| Triethyl citrate | | 1.5 | 1.5 |
| Purified Water | | 215.08 | |
| Total | | 481.6 | 24.08 |

Procedure for Coating Suspension Preparation:
  Alginic acid was weighed and kept under stirring with water for 30 minutes on an overhead stirrer to prepare 6% solution.
  Talc, triethylcitrate and colour were homogenized with remaining amount of water for 30 minutes.
  Homogenized talc suspension was added to Alginic acid suspension of step 2 and stirring was continued for further 30 mins.
  The final prepared suspension was passed through a sieve of 300 microns (60#).
  This suspension was further sprayed onto tablets in a coating pan.
Results:
  Film formation not observed.

Example 27C (Comparative)

Alginic Acid

Coating of 16 mg/cm² polymer (EUDRAGIT® NM 30D 4 mg/cm²+alginic acid 12 mg/cm²)
Formula for Coating Suspension on 300 g Tablets.

| Ingredient | Manufacturer | Quantity/Batch [g] | Solid content [g] |
| --- | --- | --- | --- |
| Alginic Acid | FMC Biopolymers | 900 | 45 |
| EUDRAGIT NM 30D | Evonik industries | 50 | 15 |
| Talc | Luznac | 7.5 | 7.5 |
| Yellow iron oxide | BASF | 0.075 | 0.075 |
| Purified Water | | 168.42 | |
| Total | | 1126.33 | 67.58 |

Procedure for Coating Suspension Preparation:
  Alginic acid was weighed and kept under stirring with water for 30 minutes on an overhead stirrer to prepare 5% solution.
  pH of alginic acid was raised to 10 by addition of 150 ml of 0.1 N NaOH.
  Talc and colour were homogenized with remaining amount of water for 30 minutes.
  Homogenized talc suspension and EUDRAGIT® NM 30D were added to Alginic acid suspension of step 2 and stirring was continued for further 30 mins.
  The final prepared suspension was passed through a sieve of 300 microns (60#).
  This suspension was further sprayed onto tablets in a coating pan.
Coating:
Suspension sprayed: 796 g
Curing parameter: No curing
Results:
  Brown colored tablets with slightly rough surface
  Enteric protection was not achieved with 96.3% w/w drug release in 0.1N HCl at 16 mg/cm² coating level

Example 28C (Comparative)

EUDRAGIT® L30 D-55

Coating of 5 mg/cm² EUDRAGIT® L 30 D-55 dry polymer
Formula for Coating Suspension on 300 g Tablets

| Ingredient | Manufacturer | Quantity/Batch [g] | Solid content [g] |
| --- | --- | --- | --- |
| EUDRAGIT ® L30 D 55 | Evonik industries | 100 | 30 |
| Talc | Luznac | 15 | 15 |
| Triethyl citrate | | 3 | 3 |
| Yellow iron oxide | BASF | 0.15 | 0.15 |
| Purified Water | | 202.85 | |
| Total | | 321 | 48.15 |

Procedure for Coating Suspension Preparation:
  Talc and colour were homogenized with 202.85 g of water for 30 minutes.
  Triethyl citrate was added to homogenized talc dispersion and homogenization was continued for further 10 minutes.
  EUDRAGIT® L30 D-55 dispersion was weighed accurately and kept for stirring on a magnetic stirrer.
  Homogenized talc suspension was added to EUDRAGIT® L30 D-55 dispersion and stirring was continued for further 10 mins.
  The final prepared suspension was passed through a sieve of 150 microns (100#).
  This suspension was further sprayed onto tablets in a coating pan.
Coating:
Coating done up to 5 mg/cm² coating level
Suspension applied: 142.1 g
Curing parameter: No curing
Results:
  Appearance—Yellow coloured tablets with smooth surface
  Enteric protection was achieved with 0% drug release in 0.1N HCl
  93%, 94% and 95% drug release was observed in 30, 45 and 60 minutes respectively in USP pH 6.8 buffer with 5 mg/cm² coating level.
  Resistance to alcohol dose dumping was not observed with higher alcohol

| | Release [%] after 2 hr. in alcoholic HCl-Plain EUDRAGIT ® L30 D 55 | |
| --- | --- | --- |
| Coating level 5 mg/cm² | 5% Alcoholic HCl 1% | 10% Alcoholic HCl 8% |
| | 20% Alcoholic HCl 72% | 40% Alcoholic HCl 93% |

Enteric resistance followed by slow drug release was observed in USP pH 5.5 buffer with 5 mg/cm² coating level with only 46%, 59% and 66% drug release observed in 30, 45 and 60 minutes respectively.

Example 29C (Comparative)

EUDRAGIT® NM 30D

Coating of 5 mg/cm² EUDRAGIT® NM 30D dry polymer
Formula for EUDRAGIT® Nm 30D Coating Suspension on 300 g Tablets

| Ingredient | Manufacturer | Quantity/Batch [g] | Solid content [g] |
| --- | --- | --- | --- |
| EUDRAGIT ® NM 30D | Evonik industries | 100 | 30 |
| Talc | Luznac | 15 | 15 |
| Yellow iron oxide | BASF | 0.15 | 0.15 |
| Purified Water | | 185.85 | |
| Total | | 301 | 45.15 |

Procedure for Coating Suspension Preparation:
  Talc and colour were homogenized with 185.15 g of water for 30 minutes.
  EUDRAGIT® NM 30D dispersion was weighed accurately and kept for stirring on a magnetic stirrer.
  Homogenized talc suspension was added to EUDRAGIT® NM 30D dispersion and stirring was continued for further 10 mins.
  The final prepared suspension was passed through a sieve of 150 microns (100#).

This suspension was further sprayed onto tablets in a coating pan.

Coating:
Coating done up to 4 mg/cm² coating level
Suspension applied: 106.5 g
Curing parameter: 24 hrs at 60° C. in a tray dryer.
Results:
 Appearance—Yellow coloured tablets with smooth surface
 Enteric resistance with 0.1% drug release in 0.1N HCl followed by only 0.6% and 0.9% drug release was observed in 45 and 60 minutes respectively in USP pH 6.8 buffer with 4 mg/cm² coating level.

| | Release [%] after 2 hr. in alcoholic HCl-Plain EUDRAGIT ® NM 30D | |
|---|---|---|
| Coating 4 mg/cm² | 5% Alcoholic HCl 5% | 10% Alcoholic HCl 11% |
| | 20% Alcoholic HCl 42% | 40% Alcoholic HCl 39% |

Examples 30-37 Overview

Examples 38-40 Overview

38 Pellet coating with a high content of glidant
39 Tablet coating with disintegration test in simulated gastric and intestinal fluid. Disintegration at pH 6.8 is sufficient for nutraceutical requirements
40 Double coating with high content of glidant and disintegrant in the inner layer Example 30

Plain Ammonium Alginate Coating on Caffeine Tablet

Formulation and Processing Methodology
Batch size: 300 g
Tablet Shape: Circular
Tablet Size: 11 mm
Polymer coating level: 5 mg/cm²
Machine used: 12 inch Ganson Coating Pan

| No. | Na-Alginate Quantity mg/cm2 | EUDRAGIT ® NM Quantity mg/cm2 | NH4-Alginate Quantity mg/cm2 | Comment | % Alginate | EtOH resistance | Other properties/remarks |
|---|---|---|---|---|---|---|---|
| 30 | — | — | 5 | NH4-Alginate | 100 | very good | Enteric protection + EtOH protection |
| 31 | | 1.75 | 5.25 | EUDRAGIT ® NM 30D:Ammonium alginate (1:3) | — | Very good | Enteric protection + EtOH protection |
| 32 | 6 | | 5 | Comparison Na-Alginate/NH4-Alginate | 100 | comparable | both with good enteric properties |
| 33 | 6 | | 5 | Comparison Na-Alginate/NH4-Alginate | 100 | comparable | almost no release with Na-Alginate at pH 6.8 + Ca$^{++}$ |
| 34 | 6 | | 5 | Comparison Na-Alginate/NH4-Alginate | 100 | comparable | both with good enteric properties |
| 35 | 12 | 4 1.75 | — 5.25 | Comparison Na-Alginate/NH4-Alginate + EUDRAGIT ® NM | 75 | comparable | both with good enteric properties |
| 36 | 12 — | 4 1.75 | — 5.25 | Comparison Na-Alginate/NH4-Alginate + EUDRAGIT ® NM | 75 | comparable | almost no release with Na-Alginate at pH 6.8 + Ca$^{++}$ |
| 37 | 12 — | 4 1.75 | — 5.25 | Comparison Na-Alginate/NH4-Alginate + EUDRAGIT ® NM | 75 | comparable | both with good enteric properties |

Formula for 5% weight gain on 300 g

| Ingredients | % Polymer | Solid content | Quantity Batch |
|---|---|---|---|
| Solid Content: 3% w/w | | | |
| Ammonium Alginate (NH$_4$-Alginate) (KIMICA ALGIN ® NH-LV, 250-550 cP at 1% w/w solution) | — | 15.00 | 15.00 |
| Talc | 50 | 7.5 | 7.5 |
| Yellow iron oxide | 0.5 | 0.08 | 0.08 |
| Water | — | — | 541.8 |
| Total | | 22.58 | 752.69 |

Procedure:
Talc and colour were homogenized in 136 gm of water for 30 minutes
Ammonium alginate was dissolved in the 405 gm of water using overhead stirrer for 30 minutes
Talc suspension was added to the ammonium alginate solution and stirred under overhead stirrer for 10 minutes.
Resulting suspension was passed through 60# sieve.
pH of final suspension: 7.15
Quantity Required for 300 gm Tablets
For 5 mg/cm$^2$ coating 663.47 suspension
Machine Parameters:
Coating Pan: 12 inch
Baffles: Present
Silicone tube (od/id): 5/3 mm
Inlet Temp: 50°-55° C.
Product Temperature: 29°-32° C.
Exhaust: ON
Blower: ON
Spray air pressure: 1.2 bar
Initial weight of 20 tabs: 8.04 gm
Required weight gain: 8.57 gm
In-Process Parameters:

| Sr. no | Time (min) | Pan RPM/ Speed | Pump RPM | Inlet Air Temp (° C.) | Product Temp (° C.) | Spray Air Pressure (bar) | Weight of 20 tablets | % weight gain |
|---|---|---|---|---|---|---|---|---|
| | | | | Process Completed | | | | |
| 1 | Initial | 22 | 2 | 55 | 34.6 | 1.2 | 8.04 | — |
| 2 | 30 | 22 | 2 | 50 | 30.1 | 1.2 | 8.10 | 0.74 |
| 3 | 60 | 22 | 2 | 50 | 29.6 | 1.2 | 8.16 | 1.49 |
| 4 | 90 | 22 | 2 | 51 | 29.2 | 1.2 | 8.28 | 2.98 |
| 5 | 120 | 22 | 2 | 50 | 30.2 | 1.2 | 8.36 | 3.97 |
| 6 | 160 | 22 | 2 | 55 | 31.6 | 1.2 | 8.48 | 5.47 |
| 7 | 200 | 22 | 2 | 53 | 31.5 | 1.2 | 8.57 | 6.6 |

Final weight gain: 8.57 gm
Pan rpm range: 22
Pump rpm range: 2
Spray rate range: 3.31 gm/min/2 RPM
Curing: 60° C. for 24 hr.
Observation:
The process was smooth without any technical problems
Results:
Appearance—Yellow coloured tablets with smooth surface
Enteric protection was achieved with 5.4% drug release in 0.1N HCl, 82.0%, 86.1% and 87.8% drug release was observed in 30, 45 minutes and 60 minutes respectively in USP pH 6.8 buffer with 5 mg/cm$^2$ coating level.
Resistance to alcohol dose dumping was also observed with 5 mg/cm$^2$ coating level at 5%, 10%, 20% and 40% alcohol (ethanol)

| | Release [%] after 2 hr in alcoholic HCl.- Ammonium alginate | |
|---|---|---|
| Coating 5 mg/cm$^2$ | 5% Alcoholic HCl 5% | 10% Alcoholic HCl 5% |
| | 20% Alcoholic HCl 4% | 40% Alcoholic HCl 2% |

The enteric resistance followed by rapid drug release behavior was retained in USP pH 4.5-5.5 buffer.
Tablet was intact in SGF and disintegration was observed within 23 minutes in SIF Example 31

EUDRAGIT® NM 30D: Ammonium Alginate (1:3) Coating on Caffeine Tablet

Formulation and Processing Methodology
Batch size: 300 gm
Tablet Shape: Circular
Tablet Size: 11 mm
Polymer coating level: 7 mg/cm$^2$
Machine used: 12 inch Pan Formula for 16% weight gain on 300 gm

| Ingredients | % Polymer | Solid content | Quantity Batch |
|---|---|---|---|
| Solid Content: 3% w/w | | | |
| EUDRAGIT ® NM 30D | — | 12 | 40 |
| Ammonium Alginate | 300 | 36 | 36 |
| Talc | 50 | 6 | 6 |
| Yellow iron oxide | 0.5 | 0.06 | 0.06 |
| Water | — | — | 1269.44 |
| Total | | 54.06 | 1802 |

Procedure:
1. Ammonium alginate was dissolved in 1400 gm of water slowly while stirring using overhead stirrer for 30 minutes.
2. Talc and colour were homogenized in remaining water for 30 minutes
3. Ammonium alginate solution was added to EUDRAGIT® NM 30D dispersion under stirring
4. Talc suspension was added to suspension of step 3 and final suspension was stirred for 10 minutes
5. Resulting suspension was passed through 60# sieve and used for spraying.
pH of final suspension: 7.18
Quantity Required for 300 gm Tablets
For 7 mg/cm$^2$ coating 694.95 gm suspension
Machine Parameters:
Coating Pan: 12 inch
Baffles: Present
Silicone tube (od/id): 5/3 mm
Inlet Temp: 50°-65° C.
Product Temperature: 30°-37° C.
Exhaust: ON Blower: ON
Spray air pressure: 1.0 bar
Initial weight of 20 tabs: 8.0 gm
Required weight gain: 8.57 gm
In-Process Parameters:

| | | | | | Process Completed | | |
|---|---|---|---|---|---|---|---|
| Sr. no | Time (min) | Pan RPM/ Speed | Pump RPM | Inlet Air Temp (° C.) | Product Temp (° C.) | Spray Air Pressure (bar) | Weight of 20 tablets | % weight gain |
| 1 | Initial | 20 | 1 | 60 | 25 | 1.0 | 8.0 | — |
| 3 | 60 | 20 | 2 | 62 | 33 | 1.0 | 8.16 | 2.0 |
| 4 | 90 | 20 | 3 | 63 | 35 | 1.0 | 8.38 | 4.75 |
| 5 | 120 | 20 | 3 | 63 | 34.8 | 1.0 | 8.53 | 6.62 |
| 6 | 140 | 20 | 3 | 63 | 35 | 1.0 | 8.56 | 6.95 |

Final Weight Gain: 8.56 gm
Pan rpm range: 20
Pump rpm range: 2-3
Spray rate range: 3.42 gm/min/2 RPM-5.04 gm/min/3 RPM
Curing: 60° C. for 24 hr.
Observation:
The process was smooth without any technical problems
Results for Example 31:
Appearance—Yellow coloured tablets with smooth surface
Enteric protection was achieved with 5.1% drug release in 0.1N HCl 86.8%, 88.7% and 89.9 drug release was observed in 30, 45 minutes and 60 minutes respectively in USP pH 6.8 buffer with 7 mg/cm² coating level.
Resistance to alcohol dose dumping was also observed with 7 mg/cm² coating level at 5%, 10%, 20% and 40% alcohol.

| | Release [%] after 2 hr in alcoholic HCl.- Ammonium alginate | |
|---|---|---|
| Coating 7 mg/cm² | 5% Alcoholic HCl 5% | 10% Alcoholic HCl 4% |
| | 20% Alcoholic HCl 3% | 40% Alcoholic HCl 3% |

The enteric resistance followed by rapid drug release behavior was retained in USP pH 4.5-5.5 buffer.
Tablet was intact in SGF and disintegration was observed within 15 minutes in SIF
Buffers and Procedure for examples 32 to 37
Preparation of Media:
1) Acid stage medium: (0.1N HCl)
For 1 L add 85 mL of concentrated hydrochloride in 900 mL of distilled water. Make up the volume till one liter and mix well.
2) Buffer stage medium: (Plain pH 6.8)
Accurately weigh and transfer 19.01 g of Trisodium Phosphate and 6.37 mL of conc. hydrochloric acid to 990 mL water. Dissolve and make up the volume till one liter and mix well. Adjust pH to 6.8±0.05 using 2N NaOH or 2N HCl.
3) Acid stage medium: (0.1N HCl with $Ca^{++}$ ions)
For 1 L add 85 mL of concentrated hydrochloride in 900 mL of distilled water. Add 0.185 g of $CaCl_2.2H_2O$ make up the volume till one liter and mix well.

4) Buffer stage medium: (Buffer pH 6.8 with $Ca^{++}$ ions)
Accurately weigh and transfer 19.01 g of Trisodium Phosphate and 6.37 mL of conc. hydrochloric acid to 1000 mL water. Add 0.185 g of $CaCl_2.2H_2O$ and dissolve and make up the volume till one liter and mix well. Adjust pH to 6.8±0.05 using 2N NaOH or 2N HCl.
Procedure:
Acid Stage: Weigh and transfer tablet of caffeine in six different dissolution jars and then perform the dissolution test as per parameters given in the method above (Acid Stage). After 2 hr remove 10 mL of aliquot and analyse as acid stage sample solution.
Buffer Stage: Transfer tablet to buffer stage medium pH 6.8. Continue the dissolution test as per parameters given in the method above (Buffer Stage). Filter the aliquots of each interval through 0.45 μm nylon membrane syringe filter discarding first few mL of the filtrate. Analyse buffer stage sample solution.
Studies were done as follows:
1) Dissolution in 0.1 N followed by pH 6.8 buffer (plain)
2) Dissolution in 1 mM Ca++ in HCl followed by 1 mM Ca++ in pH 6.8 buffer
3) Addition of 1 mM Ca++ in HCl followed by pH 6.8 buffer (without Calcium)

Examples 32 to 34

Comparison of Sodium Alginate and Ammonium Alginate in the Presence of Calcium Ions

| Example | buffer | Time | Na-Alginate 6 mg/cm² | NH₄-Alginate 5 mg/cm² |
|---|---|---|---|---|
| 32 | pH 1.2 | 0 | 0.0 | 0.0 |
| | | 120 | 6.4 | 5.4 |
| | pH 6.8 | 150 | 82.4 | 82.0 |
| | | 165 | 90.0 | 86.1 |
| | | 180 | 92.2 | 87.7 |
| 33 | pH 1.2 + $Ca^{++}$ | 0 | 0.0 | 0.0 |
| | | 120 | 5.7 | 5.6 |
| | pH 6.8 + $Ca^{++}$ | 150 | 6.5 | 73.7 |
| | | 165 | 7.0 | 86.4 |
| | | 180 | 7.8 | 88.0 |
| 34 | pH 1.2 + $Ca^{++}$ | 0 | 0.0 | 0.0 |
| | | 120 | 5.9 | 6.1 |
| | pH 6.8 | 150 | 89.9 | 72.3 |
| | | 165 | 93.8 | 82.8 |
| | | 180 | 94.7 | 88.9 |

Result: The Sodium alginate coating is sensitive to the presence of calcium in pH 6.8 buffer, while the ammonium alginate coating is not.

Examples 35 to 37

Comparison of Sodium Alginate and Ammonium Alginate with Addition of EUDRAGIT® NM in the Presence of Calcium Ions

| Example | buffer | Time | Na-Alginate + EUDRAGIT® NM (3:1) 16 mg/cm² | NH₄-Alginate + EUDRAGIT® NM (3:1) 7 mg/cm² |
|---|---|---|---|---|
| 35 | pH 1.2 | 0 | 0.0 | 0.0 |
|  |  | 120 | 4.2 | 5.1 |
|  | pH 6.8 | 150 | 73.7 | 86.8 |
|  |  | 165 | 92.9 | 88.7 |
|  |  | 180 | 94.5 | 89.9 |
| 36 | pH 1.2 + Ca⁺⁺ | 0 | 0.0 | 0.0 |
|  |  | 120 | 4.5 | 4.8 |
|  | pH 6.8 + Ca⁺⁺ | 150 | 5.2 | 72.0 |
|  |  | 165 | 5.4 | 79.0 |
|  |  | 180 | 5.8 | 82.0 |
| 37 | pH 1.2 + Ca⁺⁺ | 0 | 0.0 | 0.0 |
|  |  | 120 | 4.4 | 4.6 |
|  | pH 6.8 | 150 | 12.0 | 85.0 |
|  |  | 165 | 88.0 | 87.3 |
|  |  | 180 | 92.3 | 88.2 |

Result: The Sodium alginate+EUDRAGIT® NM coating is sensitive to the presence of calcium in pH 6.8 buffer, while the ammonium alginate+EUDRAGIT® NM coating is not.

Example 38

Potassium Alginate (200-400 cP for 1% Aqueous Solution) Pellet Formulation with 200% Talc EUDRAGIT® NM 30D: Potassium Alginate: 1:3 coating Formula for Polymer Coating Suspension on 600 g Caffeine Pellets (Size 1.0 to 1.4 mm, -Drug Load Approximately 25%)

| Ingredient | Manufacturer | Quantity/Batch [g] | Solid content [g] |
|---|---|---|---|
| Potassium alginate | FMC Biopolymers | 225 | 112.5 |
| EUDRAGIT® NM 30D | Evonik industries | 250 | 37.5 |
| Talc | Luznac | 600 | 300.0 |
| Purified Water |  | 12792.73 |  |
| Total |  | 13869.23 | 450.0 |

Procedure for Coating Suspension Preparation:
Potassium Alginate was weighed and kept under stirring with water for 60 minutes on an overhead stirrer to prepare 2% solution.
Talc and colour were homogenized with remaining amount of water for 30 minutes.
Homogenized talc suspension and EUDRAGIT® NM 30D were added to Alginate solution of step 1 and stirring was continued for further 30 mins.
The final prepared suspension was passed through a sieve of 300 microns (60#).
This suspension was further sprayed onto pellets in fluidized bed processor Coating:
Coating done up to 25% polymer level
Curing 24 hours at 60° C. in tray dryer
Results:
Appearance—Cream coloured pellets
Enteric protection was achieved with 13.9% drug release in 0.1N HCl after 120 minutes for 25% w/w polymer coating level
50.8% drug release was observed in 60 minutes in USP pH 6.8 buffer with 25% w/w polymer coating level
Resistance to alcohol dose dumping was observed with 25% w/w polymer coating level at 5%, 10%, 20% and 40% alcohol levels.

| | Release [%] after 2 hr. in alcoholic HCl-EUDRAGIT® NM 30D d.s.:Potassium Alginate (1:3) | |
|---|---|---|
| Coating | 5% Alco HCl | 10% Alco HCl |
| 25% polymer | 13% | 12% |
|  | 20% Alco HCl | 40% Alco HCl |
|  | 8% | 2% |

Example 39

Sodium Alginate (not Less than 45 cP in 1% Aqueous Solution)

Coating of 5.2 mg/cm² polymer (EUDRAGIT® NM 30D 4 mg/cm²+sodium alginate 1.2 mg/cm²)
Formula for Polymer Coating Suspension on 500 g Tablets.

| Ingredient | Manufacturer | Quantity/Batch [g] | Solid content [g] |
|---|---|---|---|
| Sodium alginate (Food grade) | Loba Chemie | 15 | 15 |
| EUDRAGIT® NM 30 D | Evonik industries | 166.67 | 50 |
| Talc | Luznac | 15 | 15 |
| Yellow iron oxide | BASF | 0.25 | 0.25 |
| Purified Water |  | 595.58 |  |
| Total |  | 802.50 | 80.25 |

Procedure for Coating Suspension Preparation:
Sodium Alginate was weighed and kept under stirring with water for 1 hour on an overhead stirrer to prepare 10% solution.
Talc and colour were homogenized with remaining amount of water for 30 minutes. Homogenized talc suspension and EUDRAGIT® NM 30D were added to Alginate solution and stirring was continued for further 30 mins.
The final prepared suspension was passed through a sieve of 300 microns (60#).
This suspension was further sprayed onto tablets in a coating pan
Coating
Suspension applied: 284.08 g
Appearance—Yellow coloured tablets with smooth surface
Dissolution results
Enteric protection was achieved with 1% drug release in 0.1N HCl
5.4%, 12.1% and 29% drug release was observed in 30, 45 minutes and 60 minutes respectively in USP pH 6.8 buffer with 5.2 mg/cm² coating level.

Disintegration results
Tablet was intact in SGF and disintegration was observed within 50 minutes in SIF

| | Release [%] after 2 hr. in alcoholic HCl-EUDRAGIT ® NM 30D d.s.:Sodium Alginate (1:0.3) | |
|---|---|---|
| Coating 5.2 mg/cm² | 5% Alco HCl 3% | 10% Alco HCl 1% |
| | 20% Alco HCl 2% | 40% Alco HCl 2% |

Resistance to alcohol dose dumping was observed with 5.2 mg/cm² polymer coating level at 5%, 10%, 20% and 40% alcohol levels.

Example 40

Pellet Formulation with Superdisintegrant Crospovidone (Polyplasdone XL) Core Formula Formula for 1600 g Caffeine Pellets

| Ingredient | Manufacturer | Quantity/ Batch [g] | Solid content [g] |
|---|---|---|---|
| Caffeine anhydrous | Aarti Industries Ltd | 640 | 640 |
| Microcrystalline cellulose (Avicel PH 101) | FMC Biopolymers | 688 | 688 |
| Crospovidone (Polyplasdone XL) | International Speciality products | 160 | 160 |
| Aerosil | Evonik industries | 80 | 80 |
| PVP K 30 | BASF | 32 | 32 |

Pellet size: 1 mm–1.4 mm
Formulation for Inner Coat
Coating of 25% Potassium alginate
Potassium Alginate (200-400 cP for 1% Aqueous Solution)
Pellet Formulation
Formula for Polymer Coating Suspension on 500 g Pellets

| Ingredient | Manufacturer | Quantity/ Batch [g] | Solid content [g] |
|---|---|---|---|
| Potassium alginate | FMC Biopolymers | 250 | 250 |
| Crospovidone (Polyplasdone XL) | International Speciality products | 87.5 | 87.5 |
| Talc | Luznac | 500 | 500 |
| Purified Water | | 20100 | |
| Total | | 20937.5 | 837.5 |

Procedure for Coating Suspension Preparation:
  Potassium Alginate was weighed and kept under stirring with water for 60 minutes on an overhead stirrer to prepare 2% solution.
  Talc and Polyplasdone XL were homogenized with remaining amount of water for 30 minutes.
  Homogenized talc suspension was added to Alginate solution of step 1 and stirring was continued for further 30 mins.
  The final prepared suspension was passed through a sieve of 300 microns (60#).
  This suspension was further sprayed onto pellets in FBP (GPCG 3.1)
Coating:
Coating done up to 25% polymer level
Suspension applied: 10468.75 g
Formulation for Outer Coat
Coating of 10% Potassium alginate
Potassium Alginate (200-400 cP for 1% Aqueous Solution)
Pellet Formulation
Formula for Polymer Coating Suspension on 500 g Pellets

| Ingredient | Manufacturer | Quantity/ Batch [g] | Solid content [g] |
|---|---|---|---|
| Potassium alginate | FMC Biopolymers | 100 | 100 |
| Talc | Luznac | 200 | 200 |
| Purified Water | | 7200 | |
| Total | | 7500 | 300 |

Procedure for Coating Suspension Preparation:
  Potassium Alginate was weighed and kept under stirring with water for 60 minutes on an overhead stirrer to prepare 2% solution.
  Talc was homogenized with remaining amount of water for 30 minutes.
  Homogenized talc suspension was added to Alginate solution of step 1 and stirring was continued for further 30 mins.
  The final prepared suspension was passed through a sieve of 300 microns (60#).
  This suspension was further sprayed onto pellets in FBP (GPCG 3.1)
Coating:
Coating done up to 10% polymer level
Suspension applied: 3750 g
Total coating done: 25% inner coat+10% outer coat=35% total coating
Results:
  Appearance—Cream coloured pellets
  Enteric protection was achieved with 13% drug release in 0.1N HCl after 120 minutes for 35% w/w polymer coating level
  59% and 70% drug release was observed in 45 and 60 minutes in USP pH 6.8 buffer with 35% w/w polymer coating level
  Resistance to alcohol dose dumping was observed with 35% w/w polymer coating level at 5%, 10%, 20% and 40% alcohol levels.

| | Release [%] after 2 hr. in alcoholic HCl-:Potassium Alginate coating | |
|---|---|---|
| Coating 35% polymer | 5% Alco HCl 13% | 10% Alco HCl 13% |
| | 20% Alco HCl 7% | 40% Alco HCl 1% |

The invention claimed is:
1. A gastric resistant pharmaceutical or nutraceutical composition, comprising:
  a core, comprising:
    a pharmaceutical or nutraceutical active ingredient and a gastric resistant coating layer on the core, wherein a release of the pharmaceutical or nutraceutical active ingredient is not more than 15% under in-vitro conditions at pH 1.2 for 2 hours in medium according to the method of USP32/NF27 with and without the addition of 40% (v/v) ethanol, and wherein the gastric resistant coating layer comprises 10 to 100% by weight of at least one salt of alginic acid which provides a 1% aqueous solution having a viscosity of 40 to 720 cP, wherein the weight gain of the coating layer is at least 3.5 mg/cm$^2$, wherein the gastric resistant coating layer comprises 0% by weight of water-insoluble polymers other than a water-insoluble polymer selected from the group consisting of a vinyl copolymer and a (meth)acrylate copolymer, wherein the gastric resistant coating layer comprises 0 to 70% by weight of one or more water-soluble cellulosic polymers, one or more water-insoluble polymers selected from the group consisting of a vinyl copolymer and a (meth)acrylate copolymer, or a mixture thereof, based on the weight of the one or more salts of alginic acid contained, and wherein said (meth)acrylate copolymer is at least one of:
(a) a methacrylate copolymer comprising free-radical polymerized units of more than 95 up to 100% by weight of $C_1$- to $C_4$-alkyl esters of acrylic or of methacrylic acid and less than 5% by weight of acrylic or methacrylic acid, and
(b) a methacrylate copolymer comprising 85 to 98% by weight of free-radical polymerized $C_1$- to $C_4$-alkyl esters of acrylic or methacrylic acid and 15 to 2% by weight of alkyl(meth)acrylate monomers with a quaternary amino group in the alkyl radical.

2. The gastric resistant pharmaceutical or nutraceutical composition according to claim 1, wherein the coating layer comprises up to 90% by weight of at least one pharmaceutical or nutraceutical acceptable excipient.

3. The gastric resistant pharmaceutical or nutraceutical composition according to claim 1, wherein a release of the pharmaceutical or nutraceutical active ingredient is at least 50% under in-vitro conditions at pH 6.8 for one hour in a buffered medium according to USP.

4. The gastric resistant pharmaceutical or nutraceutical composition according to claim 1, wherein the at least one salt of alginic acid is at least one selected from the group consisting of sodium alginate, potassium alginate, magnesium alginate, lithium alginate and ammonium alginate.

5. The gastric resistant pharmaceutical or nutraceutical composition according to claim 1, wherein the water-insoluble polymers comprise (meth)acrylate copolymers.

6. The gastric resistant pharmaceutical or nutraceutical composition according to claim 5, wherein the (meth)acrylate copolymer comprises free-radical polymerized units of more than 95 up to 100% by weight of $C_1$- to $C_4$-alkyl esters of acrylic or of methacrylic acid and less than 5% by weight of acrylic or methacrylic acid.

7. The gastric resistant pharmaceutical or nutraceutical composition according to claim 6, wherein the methacrylate copolymer comprises:
20 to 40% by weight of ethyl acrylate;
60 to 80% by weight of methyl methacrylate; and
0 to less than 5% by weight of methacrylic acid.

8. The gastric resistant pharmaceutical or nutraceutical composition according to claim 5, wherein the (meth)acrylate copolymer comprises:

85 to 98% by weight of free-radical polymerized $C_1$- to $C_4$-alkyl esters of acrylic or methacrylic acid and 15 to 2% by weight of alkyl(meth)acrylate monomers with a quaternary amino group in the alkyl radical.

9. The gastric resistant pharmaceutical or nutraceutical composition according to claim 1, wherein the at least one polymer is hydroxypropylmethyl cellulose.

10. The gastric resistant pharmaceutical or nutraceutical composition according to claim 1, wherein the core or the gastric resistant coating layer further comprises at least one pharmaceutical or nutraceutical acceptable excipient selected from the group consisting of
an antioxidant, a brightener, a binding agent, a flavouring agent, a flow aid, a fragrance, a glidant, a penetration-promoting agent, a pigment, a plasticizer, a pore-forming agent and a stabilizer.

11. The gastric resistant pharmaceutical or nutraceutical composition according to claim 1, wherein the gastric resistant pharmaceutical or nutraceutical composition is selected from the group consisting of a coated tablet, a coated minitablet, a coated pellet, a coated granule, a sachet, a capsule filled with coated pellets, powder or granules, and a coated capsule.

12. An aqueous coating solution, suspension or dispersion comprising the gastric resistant pharmaceutical or nutraceutical composition according to claim 1.

13. A process for producing the gastric resistant pharmaceutical or nutraceutical composition according to claim 1, comprising:
forming the core comprising the active ingredient by at least one method selected from the group consisting of direct compression, compression of dry, wet or sintered granules, extrusion and subsequent rounding off, wet or dry granulation, direct pelleting, by binding powders onto active ingredient-free beads or neutral cores or active ingredient-containing particles and
applying the gastric resistant coating layer in the form of an aqueous dispersion in a spray process or by fluidized bed spray granulation onto the core.

14. The gastric resistant pharmaceutical or nutraceutical composition according to claim 1, wherein the gastric resistant coating layer comprises 10 to 100% by weight of at least one salt of alginic acid which provides a 1% aqueous solution having a viscosity of 40 to 450 cP.

15. The gastric resistant pharmaceutical or nutraceutical composition according to claim 1, wherein the gastric resistant coating layer comprises 10 to 100% by weight of at least one salt of alginic acid which provides a 1% aqueous solution having a viscosity of 50 to 300 cP.

16. The gastric resistant pharmaceutical or nutraceutical composition according to claim 1, wherein the gastric resistant coating layer comprises potassium alginate.

17. The gastric resistant pharmaceutical or nutraceutical composition according to claim 1, wherein the gastric resistant coating layer comprises 70 to 90% by weight of at least one salt of alginic acid which provides a 1% aqueous solution having a viscosity of 40 to 720 cP.

18. The gastric resistant pharmaceutical or nutraceutical composition according to claim 15, wherein the gastric resistant coating layer comprises 70 to 90% by weight of at least one salt of alginic acid which provides a 1% aqueous solution having a viscosity of 50 to 300 cP.

19. The gastric resistant pharmaceutical or nutraceutical composition according to claim 1, wherein said gastric resistant coating layer comprises from greater than 0 to 70% by weight of one or more water-soluble cellulosic polymers, one or more water-insoluble polymers selected from the group consisting of a vinyl copolymer and a (meth)acrylate copolymer, or a mixture thereof, based on the weight of the one or more salts of alginic acid contained.

20. The gastric resistant pharmaceutical or nutraceutical composition according to claim 1, wherein, in gastric resistant coating layer, the at least one salt of alginic acid is at least one of sodium alginate and ammonium alginate, and
the methacrylate copolymer is present and comprises:
20 to 40% by weight of ethyl acrylate;
60 to 80% by weight of methyl methacrylate; and
0 to less than 5% by weight of methacrylic acid.

21. The gastric resistant pharmaceutical or nutraceutical composition according to claim 1, wherein, in gastric resistant coating layer, the at least one salt of alginic acid is ammonium alginate, and
the methacrylate copolymer is present and comprises:
20 to 40% by weight of ethyl acrylate;
60 to 80% by weight of methyl methacrylate; and
0 to less than 5% by weight of methacrylic acid.

* * * * *